United States Patent [19]

Greenberg et al.

[11] Patent Number: 4,851,526

[45] Date of Patent: Jul. 25, 1989

[54] 1-(4-SUBSTITUTED PHENYL)-1H-IMIDAZOLES COMPOUNDS

[75] Inventors: Stanley S. Greenberg, Morris Plains; Randall E. Lis, Stanhope, both of N.J.; William C. Lumma, Jr., Pennsburg, Pa.; Klaus Nickisch, Berlin, Fed. Rep. of Germany; Ronald A. Wohl, Morris Plains, N.J.

[73] Assignee: Schering A.G., Berlin, Fed. Rep. of Germany

[21] Appl. No.: 93,425

[22] Filed: Sep. 4, 1987

[51] Int. Cl.[4] .................. C07D 233/60; C07D 233/61
[52] U.S. Cl. ..................... 540/603; 544/139; 544/370; 546/210; 548/336; 548/341
[58] Field of Search ............... 540/603; 544/139, 370; 546/210; 548/336, 341

[56] References Cited

U.S. PATENT DOCUMENTS

| | | | |
|---|---|---|---|
| 3,708,598 | 1/1973 | Griot | 546/210 |
| 4,226,878 | 10/1980 | Iizwka et al. | 548/335 |
| 4,301,169 | 11/1981 | Yamanaka et al. | 548/336 |
| 4,567,276 | 1/1986 | Baldwin | 548/336 |
| 4,581,369 | 4/1986 | Tsuruda | 548/336 |
| 4,619,929 | 10/1986 | Thieme et al. | 544/366 |

FOREIGN PATENT DOCUMENTS 3326749  7/1983  Fed. Rep. of Germany ...... 548/341

*Primary Examiner*—Mary C. Lee
*Assistant Examiner*—Zinna Northington
*Attorney, Agent, or Firm*—Elizabeth A. Bellamy; John L. White; I. William Millen

[57] ABSTRACT

Novel 1-(4-substituted phenyl)-1H-imidazoles and their use as antiarrhythmic, anti-hypertensive and anti-ischemic agents is described. Pharmaceutical formulations containing such compounds are also discussed.

14 Claims, No Drawings

1-(4-SUBSTITUTED PHENYL)-1H-IMIDAZOLES COMPOUNDS

FIELD OF THE INVENTION

This invention relates to novel substituted phenylimidazoles and their use as antiarrhythmic, antihypertensive and anti-ischemic agents. Specifically, this invention relates to novel 1-(4-substituted phenyl)-1H-imidazoles, their pharmaceutically acceptable salts and to pharmaceutical compositions containing them as active ingredients. It also relates to the method of using these compounds primarily in the treatment of arrhythmias, especially in the treatment of arrhythmias for which class III agents are effective. Some of the compounds are also useful in the treatment of hypertension and myocardial infarction.

GENERAL DESCRIPTION OF THE INVENTION COMPOSITION-OF-MATTER ASPECT

In its composition-of-matter aspect this invention relates to novel 1-(4-substituted phenyl)-1H-imidazoles and their pharmaceutically acceptable salts. Particularly, this invention relates to novel compounds defined by the following Formula I:

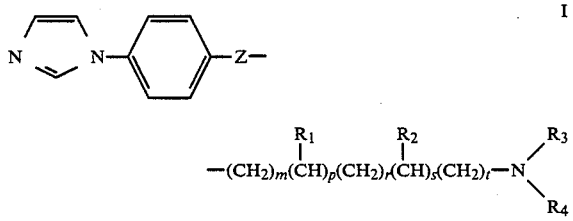

I wherein
Z is —CH$_2$, —,

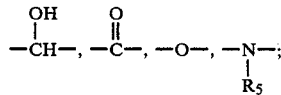

and m,p,r,s and t are the integers 0 or 1.

$R_1$ is hydrogen, lower alkyl, or collectively with $R_2$ is an alkylene chain to form a saturated carbocyclic ring of from 3 to 7 ring atoms, or collectively with $R_3$ is an alkylene chain to form a heterocyclic ring of from 4 to 7 ring atoms.

$R_2$ is hydrogen, lower alkyl, loweralkoxyloweralkyl.

$R_3$ is 2-propenyl, $C_1$-$C_8$ straight or branched chain alkyl, cycloalkyl, cycloalkyl(lower)alkyl, phenylalkyl, phenoxyalkyl, substituted phenylalkyl, substituted phenoxyalkyl, or collectively with $R_4$ forms a saturated heterocyclic ring of from 4 to 7 ring atoms which may be substituted by one or more methyl groups or collectively with $R_4$ can also be the system —CH$_2$CH$_2$O—CH$_2$CH$_2$—or

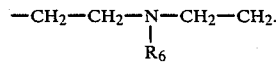

$R_3$ collectively with $R_5$ is an alkylene chain to form a piperazine or a hexahydro 1,4-diazepine ring system.

$R_4$ is hydrogen, 2-propenyl, $C_1$-$C_8$ straight or branched chain alkyl, cycloalkyl, cycloalkyl(lower)alkyl, phenylalkyl or a substituted phenylalkyl.

$R_5$ is hydrogen, 2-propenyl, $C_1$-$C_8$ straight or branched chain alkyl, cycloalkyl, cycloalkyl(lower)alkyl, phenylalkyl or a substituted phenylalkyl.

$R_6$ is hydrogen, 2-propenyl, $C_1$-$C_8$ straight or branched chain alkyl, cycloalkyl, cycloalkyl(lower)alkyl, phenylalkyl or substituted phenylalkyl.

There are provisos in the foregoing such that:

(a) when $R_1$ and $R_2$ collectively form a ring then $R_3$ cannot collectively form a ring with $R_5$, (b) when Z is —CH$_2$—then $R_1$ and $R_2$ cannot be hydrogen or lower alkyl, $R_4$ cannot be hydrogen and $R_3$ and $R_4$ cannot be $C_1$-$C_8$ straight or branched chain alkyl, (c) when Z is —O—or

then the sum of m,p,r,s and t must be at least 2, and (d) when Z is

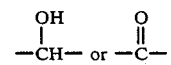

then the sum of m,p,r,s, and t must be at least 1.

Also contemplated as part of this invention are the pharmaceutically acceptable salts of the compounds of Formula I. Useful acids for this purpose include inorganic acids such as hydrobromic, hydrochloric, sulfuric, phosphoric and organic acids such as acetic, propanoic, benzoic, naphthalenecarboxylic, oxalic, succinic, malic, adipic, lactic, tartaric, citric, salicylic, methanesulfonic and p-toluenesulfonic.

It is to be understood that the definition of the compounds of Formula I encompasses all possible stereoisomers and mixtures thereof, which possess the activity discussed below. In particular, it encompasses racemic modifications and any optical isomers which possess the indicated activity.

In the foregoing Formula I, various terms are defined in the following manner. "lower" alkyl/alkoxy shall refer to a straight or branched chain of from 1 to 4 carbon atoms, for example, methyl, ethyl, propyl, butyl, isopropyl, isobutyl, tertiary butyl and sec. butyl. The term $C_1$-$C_8$ straight or branched chain alkyl shall be inclusive of such moieties as methyl, ethyl, propyl, isopropyl, butyl, isobutyl, tertiary butyl, sec. butyl, pentyl, neopentyl, hexyl, 3-methylpentyl, heptyl, 2-methylhexyl, octyl and 2-ethylhexyl. The term cycloalkyl shall refer to a saturated carbocyclic ring containing 3 to 7 carbon atoms whilst cycloalkyl(lower)alkyl shall refer to said cycloalkyl at the terminus of a 1-4 straight carbon chain. The term phenylalkyl shall refer to a phenyl group at the terminus of a $C_1$-$C_4$ straight carbon chain. The term phenoxyalkyl shall mean a phenoxy group attached to a $C_1$-$C_4$ straight chain with at least a 2 carbon separation from the nitrogen atom. The terms substituted when applied to phenylalkyl or phenoxyalkyl shall mean 1-3 substituents on the phenyl portion selected from hydrogen, chlorine, bromine, loweralkoxy, loweralkyl and trifluoromethyl.

Preferred classes of compounds embodied by this invention are those of the above general Formula I having one of the following characteristics:

(a) Z is —O—,
(b) Z is $$-\underset{\underset{R_5}{|}}{N}-,$$

(c) the sum of m+p+r+s+t is two,
(d) the sum of m, r and t is 0 and $R_1$ collectively with $R_2$ is an alkylene chain forming a saturated carbocyclic of 6 ring atoms.

The compounds which follow are some of those which serve to exemplify various aspects of the invention described herein.

(1) N,N-Diethyl-2-[4-(1H-imidazol-1-yl)phenoxy]-ethanamine.
(2) 2-[4-(1H-Imidazol-1-yl)phenyloxy]-N,N-bis-(phenylmethyl)ethanamine.
(3) 2-[4-(1H-Imidazol-1-yl)phenyloxy]-N-(phenylmethyl)ethanamine.
(4) N,N-Diethyl-N'-[4-(1H-imidazol-1-yl)phenyl]-1,2-ethanediamine.
(5) 1-[4-(1H-Imidazol-1-yl)phenyl]-4-(4-methylpiperidin-1-yl)butanone.
(6) 4-(Diethylamino)-1-[4-(1H-imidazol-1-yl)phenyl]-butanone
(7) α-[4-(1H-Imidazol-1-yl)phenyl]-4-methyl-1-piperidineethanol.
(8) 4-(1H-Imidazol-1-yl)-α-[((1-methylethyl)amino)-methyl]benzenemethanol.
(9) α-[[Ethyl(phenylmethyl)amino]methyl]-4-(1H-imidazol-1-yl)benzenemethanol.
(10) 4-[3-[4-(1H-imidazol-1-yl)phenoxy]butyl]morpholine.
(11) 1-[[2-[[4-(1H-imidazol-1-yl)phenoxy]methyl]-cyclopropyl]methyl]-4-pentylpiperazine.
(12) N-Heptyl-3-[[-4-(2methyl-1H-imidazol-1-yl)-phenoxy]methyl]-N-2-propenylcycloheptanamine.
(13) 1-[2-(4-Chlorophenyl)ethyl]-4-[[4-(1H-imidazol-1-yl)phenoxy]methyl]piperazine.
(14) 1-[4-[[1-(Cyclohexylmethyl)azetidin-3-yl]-methoxy]phenyl]imidazole.
(15) 1-[4-[[3-(2-Methylpropoxy)-2-pyrrolidin-1-yl]propoxy]phenyl]-1H-imidazole.
(16) 4-(1H-Imidazol-1-yl)-N-[(2-trifluorophenoxy)ethyl]benzenemethanamine.
(17) 4-(1H-Imidazol-1-yl)-α-[[(3-chlorophenoxyethyl)amino]methyl]benzenemethanol.
(18) N-Ethyl-N-[2-(4-methylphenoxy)ethyl]-2-[4-(1H-imidazol-1-yl)phenoxy]ethanamine.

PROCESS ASPECT

In general, the compounds of this invention may be prepared using various processes and reactants known in the art. Schemes A-H are illustrative of but not limiting for methods and procedures which are used to prepare compounds of Formula I. The choice of synthetic route is dependent on the substituents in Formula I and would be obvious to one skilled in the art.

SCHEME A

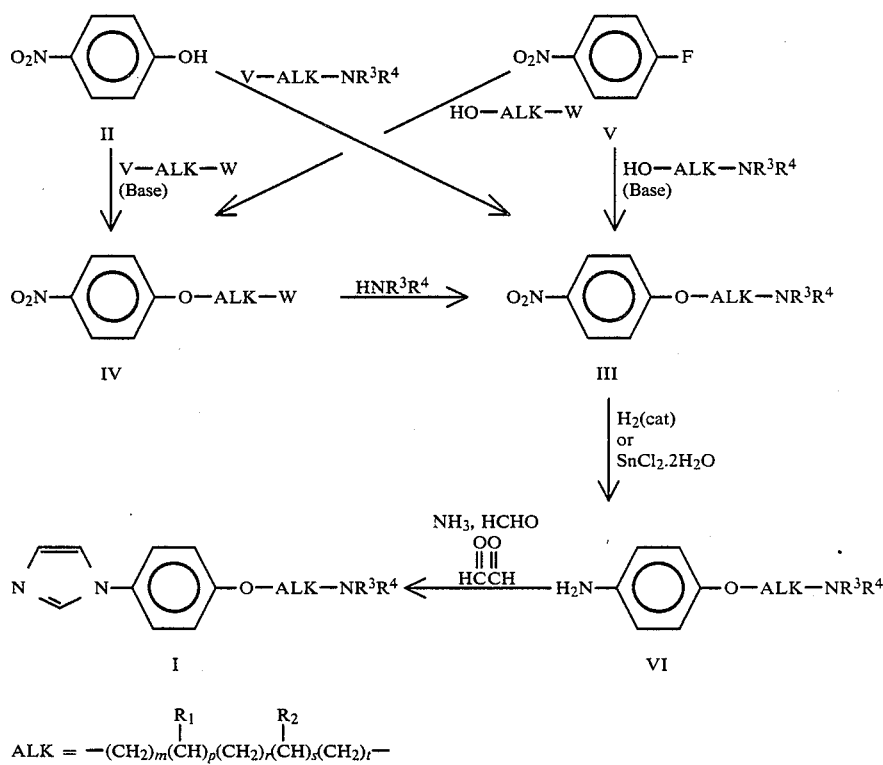

V=activating groups Cl, Br, OTs, OMs
W=activating groups Cl, Br, OTs, or OProt→O-H→OTs (OMs)
$R^4$ may be $R^{Prot}$ where $R^{Prot}$ is a protecting group (e.g. benzyl, 4-methoxybenzyl, etc.) which can be removed at the end of the synthesis to give $R^4$=H.

Outlined in Scheme A is a route for the preparation of 4-(1H-imidazol-1-yl)phenyl ethers of Formula I (Z is —O—). 4-Nitrophenol II is reacted with an ω-activated tertiary amine in the presence of a base in a suitable solvent to provide the ether III. The activating group may be a halogen or a sulfonate ester. Suitable bases are sodium hydroxide, potassium carbonate, sodium hydride or sodium alkoxides; appropriate solvents are tetrahydrofuran, acetone, methanol, ethanol, dimethylformamide, 1,2-dimethoxyethane or dimethylsulfoxide. The choice of base/solvent combinations are apparent to those skilled in the art. The reaction temperature for the above alkylation may range from about 0° to 150° C., preferably at about 60° C. In an alternate approach the amino ether III described above may be prepared in two steps. The nitrophenol II may be reacted with an α,ω-activated alkylene moiety under conditions similar to those described above, to give compound IV. The resulting ω-activated alkyl ether IV may be reacted with an excess of a secondary amine either neat or in an appropriate solvent (tetrahydrofuran, acetonitrile, methanol, ethanol, dimethylformamide or dimethylsulfoxide) at a temperature from about 0° to 150° C. preferably at about 60° C. to 80° C. to provide the amino ether III. In yet another approach 1-fluoro-4-nitrobenze V may be reacted in one step with an amino alcohol to give III or in two steps with an ω-activated alcohol, then with secondary amine to give III via IV. Reaction conditions are similar to those described above. The nitrophenyl ether III can be reduced either catalytically under a hydrogen atmosphere or chemically to give aminophenyl ether VI by a variety of processes known in the art. For example, hydrogenation of III can be carried out over catalysts such as, palladium on carbon, platinum oxide or Raney Nickel in a suitable solvent (methanol, ethanol, water) at a hydrogen pressure of 1 to 4 atom at temperatures of about 0° to 50° C., preferably at about 25° C. In an alternate procedure compound VI may be produced by reduction of III using tin (II) chloride dihydrate in refluxing ethanol or ethyl acetate. The Debus reaction of aniline VI with ammonia, formaldehyde and a glyoxal provides the 4-(1H-imidazol-1-yl)phenyl ethers of formula I. In this reaction the components are generally used in a 1:1:1:1 ratio. A mixture of aniline VI and ammonia and a second mixture of the aldehyde and α-diketone are added simultaneously to the reaction vessel. The solvents employed are generally water or water/alcohol mixtures. The temperature of the reaction mixture is usually maintained from 20° to 150° C., preferably from about 70° C. to 120° C.

In the case where $R^4$ of formula I is hydrogen, $R^4$ may be replaced during the synthetic operations with $R^{Prot}$, where $R^{Prot}$ is a protecting group (e.g. benzyl or 4-methoxybenzyl, etc.) which may be removed at the end of the synthetic sequence to provide $R^4 = H$.

In the α,ω=diactivated compounds, e.g. V-ALK-W, the activating group W may be masked (protected) in order to allow selective reaction at the V group. For example, W can be a protected alcohol (e.g. as the tetrahydropyranyl ether), which after reaction at V can be deprotected and reacted with tosyl chloride to give W as the tosyloxy group.

SCHEME B

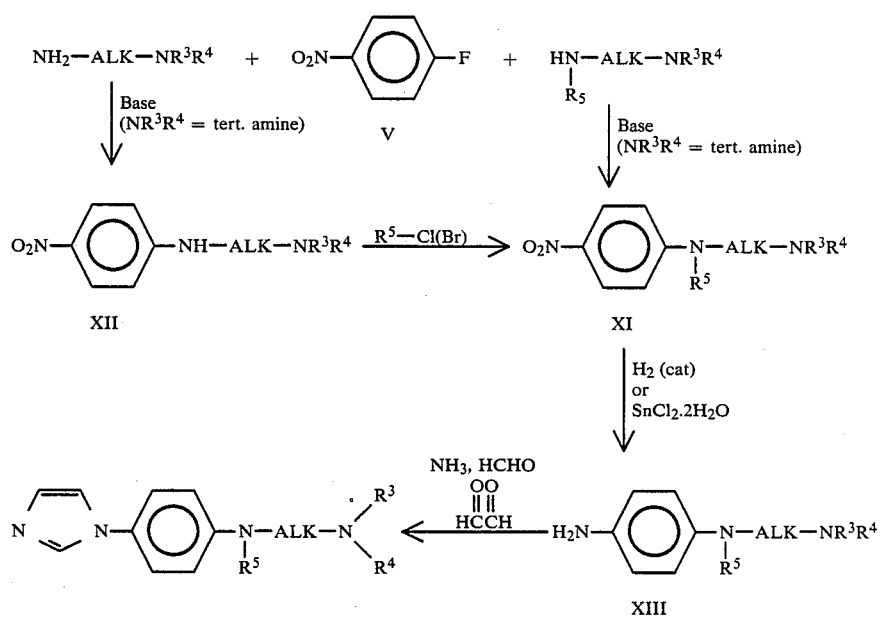

Scheme B outlines a method for preparing compounds of the invention wherein Z is

Fluoronitroaniline V is reacted in either one or two steps to give N-(ω-aminoalkyl)-4-nitroaniline of Formula XI. In the one step route a N,N,N'-trisubstituted diamine is reacted with V to afford XI directly. The reaction is generally carried out either neat or in an aprotic solvent such as acetonitrile, propionitrile, tetrahydrofuran, N,N-dimethylformamide at a temperature from about 25° C. to 150° C., preferably at about 60° C. In the two step route, V is reacted with an N,N-disubstituted alkanediamine to give compound XII. Compound XII is further reacted with a second alkylating agent $R^5$—Cl to provide intermediate XI. Reaction conditions for the two step route are similar to those described above for the one step route. It may at times be desirable to add a base to the reaction mixture to facilitate the reaction. This may be done by using two equivalents of the diamine or by adding a suitable acid scavenger such as potassium carbonate. Reduction of XI to XII and the Debus reaction of XIII to compounds of Formula I (Z is

is carried out as described in Scheme A.

An alternate synthesis of the compounds of Formula I wherein Z is

is described in Scheme C.

SCHEME C

1-Fluoro-4-nitrobenzene V is reacted with a primary amine ($H_2NR^5$) under conditions similar to those described above to give the nitroaniline XIV. The aniline is then reacted with either an ω-amino activated acyl derivative such as an acid chloride, mixed anhydride or a DDC activated acid or an ω-activated acyl derivative such as an ω-haloacyl halide, etc. The choice of reaction conditions and solvents depends on the acyl derivative employed and are known in the art. In the case of the ω-amino activated acyl derivatives reaction with XIV produces an ω-amino-N-(4-nitrophenyl)amide XV directly. Reaction of the ω-activated acyl derivative with XIV provides an ω-activated N-4-nitrophenyl)amide XVI, which when reacted with a secondary amine $HNR^3R^4$ under conditions described above produces XV. Nitro compound XV is reduced to XVII and converted to the 4-(1H-imidazol-1-yl)anilide XVIII as described previously. Lithium aluminum hydride reduction of XVIII affords compounds of Formula I (Z=$NR^5$). The hydride reduction is generally carried out in a solvent such as diethylether, 1,2-dimethoxyethane or tetrahydrofuran at temperatures from about 0° to 100° C., preferably at about 60° C.

SCHEME D

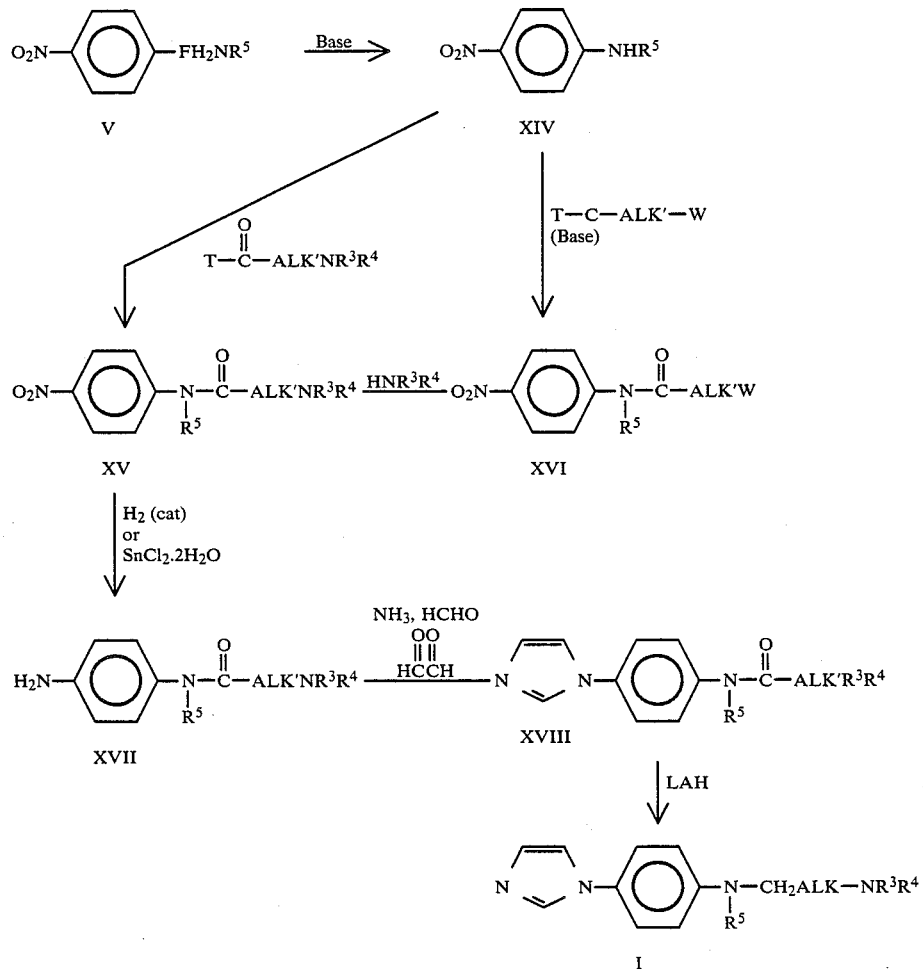

ALK = ALK'CH₂
T = Activating group (eg. Cl, OCH₃ etc.)
W = Cl, Br, I, OTs, OMs
NR³R⁴ may be replaced by NR³R^Prot as necessary

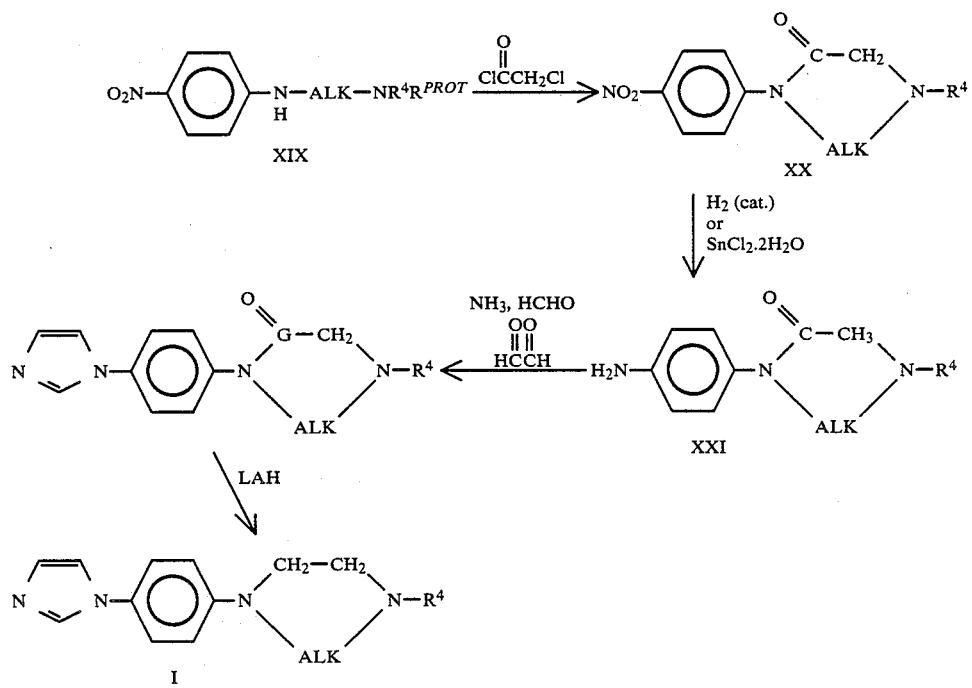

Scheme D describes a method whereby compounds of Formula I where $R^3$–$R^5$ form a ring, can be prepared. In Scheme D an N'-(4-nitrophenyl)-N-substituted-N-protected alkanediamine XIX is acylated with chloroacetyl chloride with ring closure to give the cyclic derivative XX. In XIX $R^{Prot}$ can be benzyl, 4-methoxybenzyl or 3,4-dimethoxybenzyl. The reaction is generally carried out in acetonitrile or propionitrile. The addition of the acid chloride is carried out at a temperature from about 0° C. -30° C. preferably at about 20° C. After work up the acylated material is heated at reflux to effect the ring closure. Conversion of XX to compounds of Formula I ($R^3$–$R^5$ form a ring) via intermediates XXI and XXII is carried out as described previously.

SCHEME E

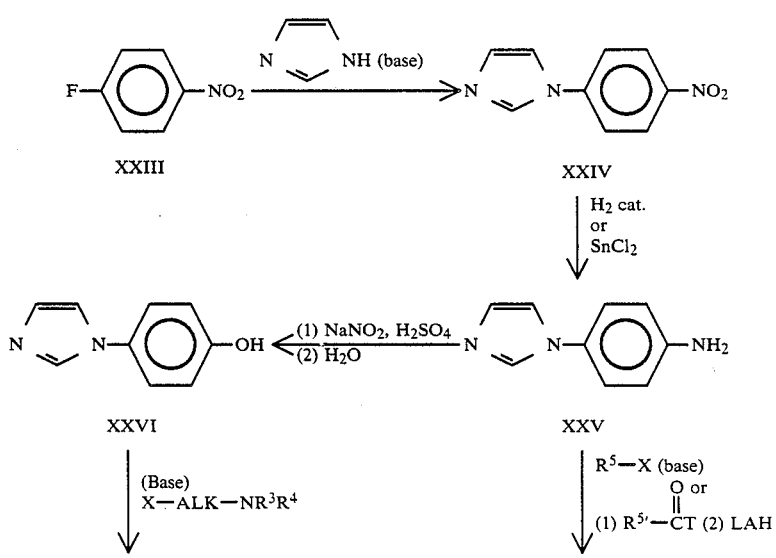

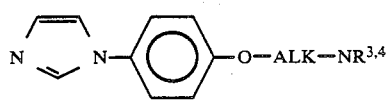

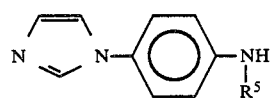

$R^5$—$CH_2$=$R^5$

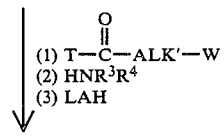

XXVII

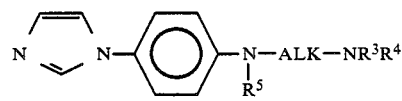

(1) T—C(=O)—ALK'—W
(2) $HNR^3R^4$
(3) LAH

Yet another method for preparation of compounds of Formula I is shown in Scheme E. In this route the imidazole moiety is inserted at the beginning of the preparation sequence. 1-Fluoro-4-nitrobenzene XXIII is reacted with the appropriate imidazole. The reaction is generally carried out in a solvent such as acetonitrile, propionitrile, N,N-dimethylformamide or dimethylsulfoxide at a temperature from about 50° C. to 150° C., preferably at a temperature from 80° C. to 100° C. The resulting 1-(4-nitrophenyl)imidazole XXIV is reduced under standard conditions to aniline XXV. Aniline XXV is converted to phenol via diazotization followed by reaction of the diazonium salt with water. The diazotization reaction is carried out by the addition of a solution of sodium nitrite in water to a cold solution of aniline XXV in aqueous sulfuric acid. The temperature of the mixture is held below 5° C. during the diazotization. The solution of diazonium salt is warmed to ca. 50° C. to effect the reaction with water to give XXVI. Alternatively, the cold solution of diazonium salt may be added dropwise to a boiling solution of aqueous sulfuric acid to obtain phenol XXVI. Aniline XXV may be used to prepare compounds of Formula I ($Z=NR^5$) in a manner similar to those described in Scheme D. Note that $R^5$ may be introduced by either a direct alkylation or in selected cases by acylation with a precursor $R^{5'}$—COT wherein $R^5=R^{5'}$—$CH_2$ and T is an activating group followed by lithium aluminum hydride reduction to obtain XXVII. Phenol XXVI may be used to prepare compounds of Formula I ($Z=O$) in a manner similar to Scheme A.

In all cases where amines are employed in reactions or where water reactive reagents are employed it is beneficial to run the reactions under an inert (nitrogen or argon) atmosphere.

SCHEME F

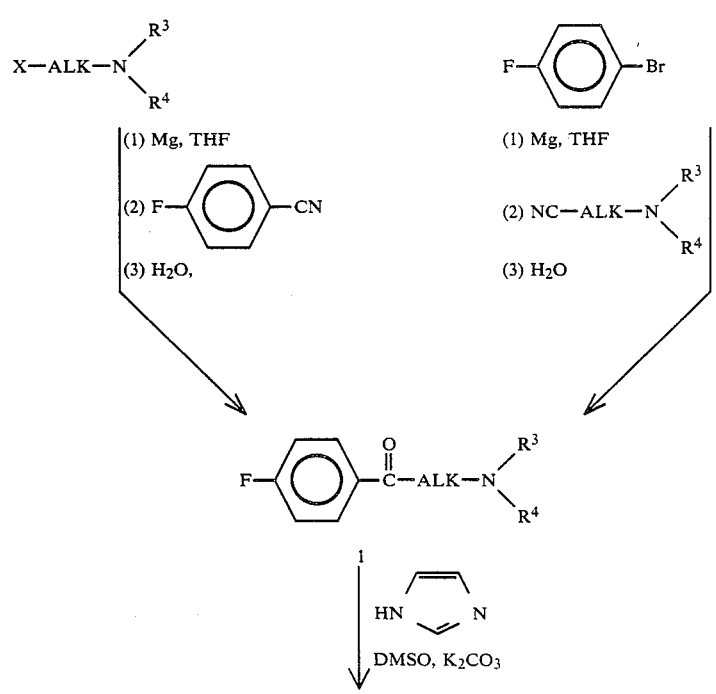

-continued

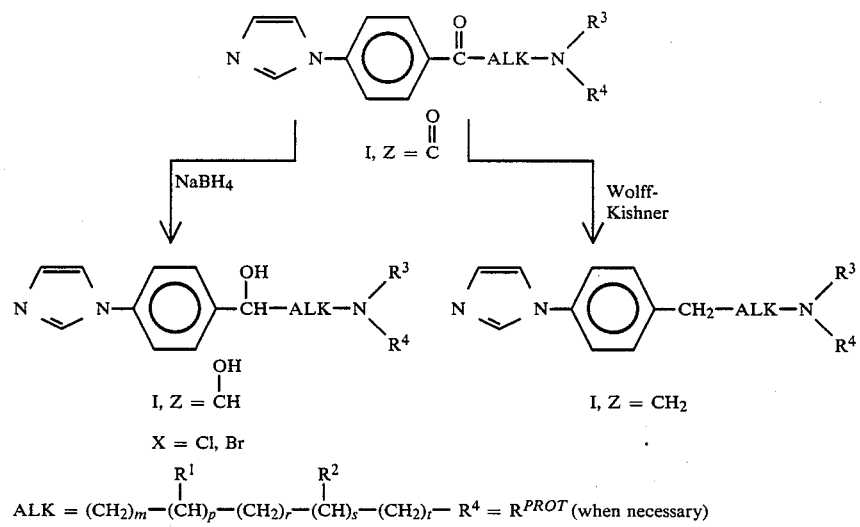

ALK = $(CH_2)_m-(CH)_p-(CH_2)_r-(CH)_s-(CH_2)_t-$  R⁴ = R^{PROT} (when necessary)

For compounds of Formula I wherein m+p+r+s+t ≧2 the methods outlined in Scheme F are appropriate. Intermediate 1 in Scheme F may be prepared by either of two routes both employing the Grignard reaction. In the first route an ω-halo (chlorine or bromine) alkyl tertiary amine is reacted with magnesium metal in a solvent such as diethyl ether, tetrahydrofuran or dimethoxyethane to form the Grignard reagent. The reaction is initiated by standard methods. The reaction is generally carried out at the reflux temperature of the solvent. When the formation of the Grignard reagent is complete 4-fluorobenzonitrile is added and heating continued for 1-5 hr. At the completion of the reaction it is quenched with water to hydrolyze the intermediate amine to the desired ketone 1. In the second route the Grignard reagent is prepared from 1-bromo-4-fluorobenzene and reacted with an ω-aminoalkylnitrile under conditions similar to those described above to give intermediate 1. For those instances in compounds of Formula I wherein R⁴=hydrogen, R⁴ is replaced by a protecting group (R^{Prot}) such as benzyl which can be removed as the last step of the sequence to afford R⁴=H. Reaction of 1 with imidazole in dimethylsulfoxide in the presence of potassium carbonate provides compounds of Formula I wherein Z is

The reaction is carried out at a temperature from about 25°-180° C. preferably at 140°-165° C. Compounds of Formula I Z is

can be reduced to the corresponding alcohol I, Z is

by a variety of methods known in the art (e.g. lithium aluminum hydride, sodium borohydride or catalytic hydrogenation). In the example shown in the scheme the ketone is reduced to the alcohol with sodium borohydride. These reactions are generally carried out in alcoholic solvents (methanol, ethanol or isopropyl alcohol) at a temperature from about —10°—50° C. preferably at about 0° C. The reduction of I, Z is

to I, Z is —CH₂—may be carried out by a variety of procedures known in the art (Wolff-Kishner reduction, Clemmensen reduction or catalytic hydrogenation). In the example shown in Scheme F ketone I(Z is

is reduced by the Wolff-Kishner method. The compound I, Z is

is heated with excess hydrazine and potassium hydroxide for about 3-5 hr at 100° C. The temperature is slowly raised to about 180°-200° C. and heating continued for about 3-5 hr.

SCHEME G

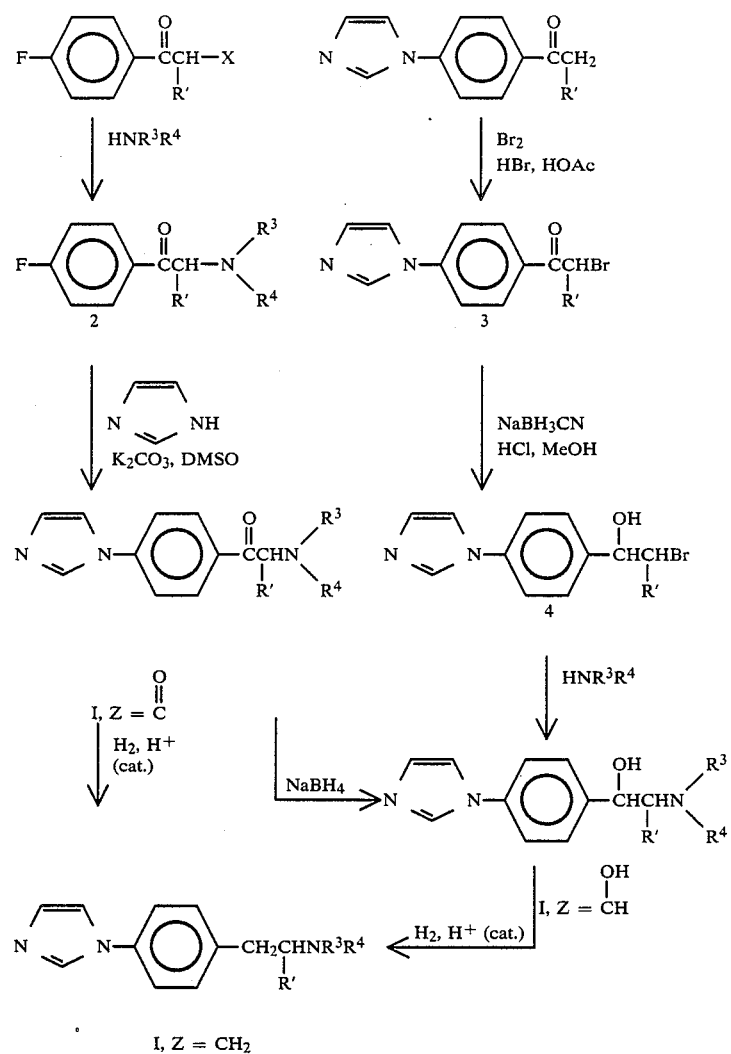

Scheme G is illustrative of methods which can be used to prepare compounds of Formula I wherein m+p+r+s+t =1. Two routes are outlined in Scheme G. In the first approach an α-halo-4-fluorophenyl ketone is reacted with a secondary amine to give amino ketone 2. The reaction is generally carried out in a solvent such as methanol, ethanol, isopropyl alcohol, diethyl ether, tetrahydrofuran, acetonitrile or N,N-dimethylformamide at a temperature from about 20° C. to 140° C. preferably at about 40°–80° C. When necessary a base such as potassium carbonate may be used to facilitate the reaction. Compound 2 is further reacted with imidazole in dimethylsulfoxide in the presence of potassium carbonate as described above for Scheme F to provide compounds of Formula I(Z is

).

The ketone may be reduced with sodium borohydride as described previously to provide I(Z is

).

Both the ketones and alcohols of Formula I(Z is

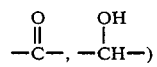)

can be hydrogenated catalytically to provide compounds of Formula I wherein Z is —CH$_2$—. The preferred catalyst is palladium. The reaction is generally run in an alcohol solvent (methanol, ethanol) with 1–3 equivalents of acid (HCl, H$_2$SO$_4$) at pressure from 1–5 atm at a temperature from about 25°–80° C. Compounds of Formula I(Z is

)

may also be reduced by Wolff-Kishner or Clemmensen reduction procedures. In the second route a 4-(1H- imidazol-1-yl)phenyl ketone is brominated at the α-position with bromine in a mixture of hydrogen bromide and acetic acid to afford 3.

The reaction is generally run at temperatures from about 15° to 50° C., generally at about 20°–25° C. Compound 3 is reduced to the bromo alcohol 4 with sodium cyanoborohydride in methanol. The reaction is carried out at pH=4–6 at room temperature. Reaction of bromo alcohol 4 with a secondary amine under conditions described in Scheme A provides compounds of Formula I(Z is

As discussed in Scheme F R⁴ may be replaced by $R^{Prot}$ when necessary.

SCHEME H

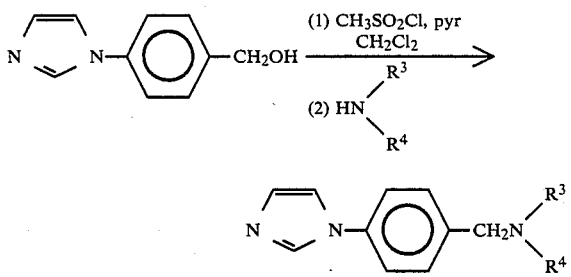

Scheme H is illustrative of the method used to prepare compounds of formula I wherein $Z=CH_2$ and m+p+r+s+t all equal O. A 4-(1H-imidazol-1-yl)benzenemethanol is reacted with methanesulfonyl chloride (other sulfonyl chlorides or anhydrides may also be used - e.g. tosyl chloride, methanesulfonic anhydride, benzenesulfonyl chloride) in the presence of a base such as pyridine, collidine, picoline or 4-(dimethylamino)-pyridine in an aprotic solvent such as methylene chloride, chloroform or acetonitrile. The reaction is run at a temperature from about −10° to 80° C. preferably adding the sulfonyl halide at 0° C. and then allowing the mixture to warm to 20°–25° C. Stirring is continued for 1 to 24 hr after the addition, then a secondary amine is added to the intermediate sulfonate ester and stirring continued for 1–24 hr. Workup affords compounds of Formula I where Z is —CH₂—and m+p+r+s+t equal O.

Certain compounds in this invention will have asymmetric carbon atoms, and as such, the possibility exists for preparation of single enantiomers. Both racemic modifications and optically active materials are contemplated as part of this invention. Optically active materials may be obtained by resolution of the racemate of compounds of Formula I or by resolution of optically active intermediates during the synthesis of compounds of Formula I by standard methods known in the art or by asymmetric synthesis.

METHOD-OF-USE AND PHARMACEUTICAL COMPOSITION ASPECT

The novel 1-(4-substituted phenyl)-1H-imidazoles of Formula I of this invention and their pharmaceutically acceptable salts are antiarrhythmic, anti-ischemic and anti-hypertensive agents. These compounds are especially useful in the treatment of a variety of cardiovascular disorders and cardiac arrhythmias, more especially, these compounds will be useful as Class III antiarrhythmic agents. Still further they will be useful as anti-anginal and anti-hypertensive agents.

In 1970, Vaughan Williams devised his, by now well known, method for classifying various antiarrhythmic agents. Generally speaking, Class I agents typified for example by flecainide, lidocaine or mexiletine are local anesthetics on nerve and myocardial membranes thereby slowing conduction which decreases the propagation of ectopic (premature) beats and suppresses the tendency of damaged cells to initiate ectopic beats. The Class II agents are the so-called β-blockers best exemplified by propranolol. The Class III agents represented by bretylium or amiodarone have little or no effect on conduction, in fact, they are quite independent of conduction. They prolong the action potential duration of the heart cells thus increasing the time interval in which the heart cells are unexcitable (refractory period) without slowing conduction or changing the excitability of the cardiac cells.

Generally, after a myocardial infarct a patient is treated with a Class I agent because cardiac cells in the border zone of the infarcted region of the heart are electrically unstable, giving rise to ectopic beats resulting in the appearance of numerous PVC's (premature ventricular contractions). As the patients' infarct heals the tissue substrate for arrhythmia may change and potentially a re-entrant pathway may be established leading to ventricular tachycardias - which condition may be treated with a Class III agent.

The compounds of the invention were tested in several biological procedures to analyze their type of antiarrhythmic effect. For instance, utilizing standard electrophysiological techniques, the resting potential, amplitude, duration, rate of rise of phase O (depolarization) of the action potential were measured in normal canine Purkinje fibers. The compounds of this invention (for example, N,N-diethyl-2-[4-(1H-imidazol-1-yl)phenoxy]ethanamine) in this screen demonstrated an increase in action potential duration without a decrease in the rate of rise of phase O and thus were designated Class III antiarrhythmic agents. Therefore, there is provided by this invention a method for treating arrhythmias which comprises administering to a mammalian subject suffering from arrhythmias and in need of treatment or to a mammalian subject suspected of developing said arrhythmias an effective amount for treating such arrhythmias of a compound of this invention.

As stated previously, certain of the compounds exhibit other cardiac, cardiovascular properties. For instance, the compound 1-[4-(1H-imidazol-1-yl)phenyl]-4-(methylpiperidin-1-yl)butanone, when tested in the conscious dog, exhibited blood pressure reduction. This coupled with an observed CNS activating profile demonstrated that said blood pressure lowering could be accomplished without concomitant CNS depressant effects. This compound in the conscious spontaneously hypertensive rat exhibited a biphasic effect with blood pressure lowering at 30 μg/kg (p.o.) and a rise in blood pressure and heart rate at 30 mg/kg (p.o.). With this vascular profile it is envisioned that this compound could be utilized in hypertension.

On the other hand, for instance, the compound 4(diethylamino)-1-[4-(1H-imidazol-1-yl)phenyl]butanone exhibited in the conscious spontaneously hypertensive rat a lowering of blood pressure and heart rate at 10 mg/kg.

In the pentobarbital anesthetized dog, the compound exhibited a bradycardiac effect at 3 mg/kg and at 10 and 30 mg/kg i.v. decreased both blood pressure and heart rate without compromising coronary blood flow. This compound should be useful in the treatment of angina.

For whatever therapeutic indication is necessary, the compounds of this invention can be formulated in a therapeutically effective pharmaceutical composition and may be administered orally or parenterally. The dosage administered will be dependent on the subject being treated, the route of administration and the type and severity of the arrhythmia or other cardiac/cardiovascular event being prevented or reduced.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention for example, N,N-diethyl-2-[4-(1H-imidazol-1-yl)phenoxy]ethanamine in the amount of about 1 to about 500 mg. Such formulation can be administered orally at the dose of about 1 to 4 capsules per day or more often as needed, depending upon the particular condition and subject being treated. For parenteral administration a compound of this invention can be formulated as an intramuscular or intravenous medicament but is not limited thereto. In the case of treatment of a patient suffering from severe cardiac arrhythmias, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. A typical formulation suited to intravenous or intramuscular administration may contain one of the compounds of this invention in the amount of about 50 to 150 mg and a solubilizing agent and sufficient sterile water to bring the volume to about 5 mL-100 mL. Such formulation can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The pharmaceutical preparations of the compounds of this invention may optionally, additionally contain one or more other pharmaceutically active substances. Some of the substances envisioned are vasodilators such as glycerol trinitrate, pentaerythirtol tetranitrate and carbochromen; diuretic agents, such as chlorothiazide; heart tonics, such as digitalis preparations; hypotensive agents, such as Rauwolfia alkaloids and guanethidine; bronchodilators and sympathomimetic agents, such as isoprenaline, orciprenaline, adrenalin and ephedrine; α-adrenergic blocking agents, such as phentolamine; β-adrenergic blocking agents, such as propranolol and other antiarrhythmic agents such as quinidine.

This invention described hereinabove is illustrated below in the Preparations and Examples, which, however, is not to be construed as limiting the scope of this invention.

PREPARATIONS

Preparation 1

α-Methyl-4-morpholinepropanol

To 100 mL of CH$_3$CN is added morpholine (9.6 g, 0.11 mol) and 4-chloro-2-butanol (11 g, 0.1 mol). Heat the reaction at reflux and monitor the reaction by thin-layer chromatography. Upon completion of the reaction remove the solvent and add saturated aqueous sodium bicarbonate and ether. Separate the layers and dry the organic phase over Na$_2$SO$_4$. Filter off the drying agent and evaporate the solvent in vacuo to obtain the title compound.

Preparation 2

4-[3-(4-Nitrophenoxy)butyl]morpholine

To 100 mL of DMF is added α-methyl-4-morpholinepropanol (15.9 g, 0.1 mol) and 7.2 g (50% in mineral oil, 0.15 mol) of NaH followed by 14.1 g (0.1 mol) of 1-fluoro4-nitrobenzene. Heat the reaction at 80° C. and monitor the reaction by thin-layer chromatography. Upon completion of the reaction add 100 mL of water and extract with ether. Dry the organic phase over Na$_2$SO$_4$. Filter off the drying agent and evaporate the solvent in vacuo to obtain the title compound.

Preparation 3

4-[[1-Methyl-3-(morpholin-4-yl)propyl]-oxy]benzenamine

To 50 mL ethanol is added 28 g (0.1 mol) of 4-[3-(4-nitrophenoxy)butyl]morpholine and 0.5 g of Pd(OH)$_2$. The mixture is hydrogenated at 30 psi. Monitor the reaction by thin-layer chromatography. Upon completion remove the catalyst by suction filtration through celite. Remove the solvent in vacuo to obtain the title compound.

Preparation 4

2-[(4-Pentylpiperazin-1-yl)carbonyl]cyclopropane-carboxylic acid

To 100 mL of ethanol is added 1-pentylpiperazine (15.6 g, 0.1 mol) and 11.2 g (0.1 mol) of 3-oxabicyclo[3.1.0]-hexane-2,4-dione. Reflux the reaction and monitor by thin-layer chromatography. Upon completion remove the solvent in vacuo to obtain the title compound.

Preparation 5

2-[(4-Pentylpiperazin-1-yl)methyl]cyclopropanemethanol

To 100 mL of tetrahydrofuran is added 24.0 g (0.1 mol) of 2-[(4-pentylpiperazin-1-yl)carbonyl]cyclopropanecarboxylic acid and 13.6 g (0.4 mol) of lithium aluminum hydride. Reflux the reaction and monitor by thin-layer chromatography. Upon completion add 14 mL of H$_2$O, 14 mL of 15% aqueous NaOH, and 42 mL of H$_2$O. Remove the precipitate by suction filtration through celite and remove the solvent in vacuo to obtain the title compound.

Preparation 6

1-[[2-[(4-Nitrophenoxy)methyl]cyclopropyl]methyl]-4-pentylpiperazine

In a manner similar to Preparation 2, react 2-[(4-pentylpiperazin-1-yl)methyl]cyclopropanemethanol to obtain the title compound.

Preparation 7

4-[[2-[(4-Pentylpiperazin-1-yl)methyl]cyclopropyl]methoxy]benzenamine

In a manner similar to Preparation 3, hydrogenate 1-[[2-[(4-nitrophenoxy)methyl]cyclopropyl]methyl]-4-pentylpiperazine to obtain the title compound.

Preparation 8

N-(2-propenyl)heptanamine

To 100 mL of methanol is added 2-propenylamine (5.7 g, 0.1 mol), 11.4 g (0.1 mol) of heptaldehyde, and 12 g (0.2 mol) of sodium cyanoborohydride. The pH is adjusted to six with concentrated HCl. Monitor the reaction by thin-layer chromatography. Upon completion, add concentrated HCl until gas evolution ceases. Add 300 mL of $H_2O$ and extract once with 200 mL of ether. Add 1N NaOH to the aqueous solution until it is basic and extract twice with 200 mL of ether. Dry the organic phase over $Na_2SO_4$. Filter off the drying agent and evaporate the solvent in vacuo to obtain the title compound.

Preparation 9

3-Oxocycloheptanecarbonitrile

To 100 mL of toluene add 2-cyclohepten-1-one (11.0 g, 0.1 mol) and 200 mL (1M solution in toluene, 0.2 mol) of diethylaluminum cyanide. Monitor the reaction by thin-layer chromatography. Upon completion add 1M aqueous HCl until gas evolution ceases. Extract twice with 100 mL of ether. Dry the organic phase with $Na_2SO_4$. Filter off the drying agent and evaporate the solvent in vacuo to obtain the title compound.

Preparation 10

3-[Heptyl(2-propenyl)amino]cycloheptanecarbonitrile

In a manner similar to Preparation 8, react 3-oxocycloheptanecarbonitrile with N-(2-propenyl)heptanamine and sodium cyanoborohydride to obtain the title compound.

Preparation 11

3-[Heptyl(2-propenyl)amino]cycloheptanecarboxylic acid

To 100 mL of 6N aqueous HCl add 3-[heptyl(2-propenyl)amino]cycloheptanecarbonitrile (27.6 g, 0.1 mol). Reflux the reaction and monitor by thin-layer chromatography. Upon completion remove the solvent in vacuo. Dissolve the residue in water and add 4.0 g (0.1 mol) of sodium hydroxide. Remove the solvent in vacuo and 100 mL methylene chloride to the residue. Remove the solid by suction filtration through celite and remove the solvent in vacuo to obtain the title compound.

Preparation 12

3-[Heptyl(2-propenyl)amino]cycloheptanemethanol

In a manner similar to Preparation 5, react 3-[heptyl-(2-propenyl)amino]cycloheptanecarboxylic acid with lithium aluminun hydride to obtain the title compound.

Preparation 13

N-Heptyl-3-[-4-nitrophenoxy)methyl]-N-(2-propenyl)-cycloheptanamine

In a manner similar to Preparation 2, react 3-[heptyl(2-propenyl)amino]cycloheptanemethanol with 4-fluoronitrobenzene to obtain the title compound.

Preparation 14

3-[(4-Aminophenoxy)methyl]-N-heptyl-N-(2-propenyl)cycloheptanamine

In a manner similar to Preparation 3, hydrogenate 3-[(2-chloro-4-nitrophenoxy)methyl]-N-heptyl-N-(2-propenyl)cycloheptanamine to obtain the title compound.

Preparation 15

4-Chlorobenzeneacetyl Chloride

To 100 mL of chloroform is added 4-chlorobenzeneacetic acid (17 g, 0.1 mol) and 24 g (0.2 mol) of thionyl chloride. Reflux the reaction mixture for 3 hours and remove the solvent in vacuo to give the title compound.

Preparation 16

1-(4-Chlorophenylacetyl)-4-(hydroxymethyl)piperidine

To a solution of 5.76 g (0.05 mol) of 4-piperidinemethanol and 4.75 g (0.06 mol) of pyridine in 50 mL of methylene chloride cooled to 0° add dropwise a solution of 10.4 g (0.055 mol) of 4-chlorobenzeneacetyl chloride in 25 mL of methylene chloride. When the addition is complete stir the reaction overnight at room temperature. After this time add 25 mL of 2N hydrochloric acid. Separate the layers and wash the methylene chloride layer with two 50 mL portions of saturated sodium bicarbonate solution and 25 mL of saturated sodium chloride solution then dry the methylene chloride layer over anhydrous sodium sulfate. Filter the drying agent and remove the solvent in vacuo to obtain the title compound.

Preparation 17

1-[2-(4-Chlorophenyl)ethyl]-4-piperidinemethanol

In a manner similar to Preparation 5, react 1-[2-(4-chlorophenyl)acetyl]-4-(hydroxymethyl)piperidine with lithium aluminum hydride to obtain the title compound.

Preparation 18

1-[2-(4-Chlorophenyl)ethyl]-4-[(4-nitrophenoxy)methyl]piperidine

In a manner similar to Preparation 2, react 1-[2-(4-chlorophenyl)ethyl]-4-piperidinemethanol with 1-fluoro4-nitrobenzene to obtain the title compound.

Preparation 19

4-[[1-[2-(4-Chlorophenyl)ethyl]piperidin-4-yl]methoxy]benzenamine

In a manner similar to Preparation 3, hydrogenate 1[2-(4-chlorophenyl)ethyl]-4-[(4-nitrophenoxy)methyl]-piperidine in acetic acid and hydrochloric acid over palladium on carbon to obtain the title compound.

Preparation 20

2-[[(Cyclohexylmethyl)amino]methyl]-1,3-propanediol

In a manner similar to Preparation 8, react cyclohexanecarboxaldehyde with 2-aminomethyl-1,3-propanediol to obtain the title compound.

Preparation 21

1-Cyclohexylmethyl-3-azetidinemethanol

To 100 mL of carbon tetrachloride add 19.2 g (0.1 mol) of 2-[(cyclohexylmethylamino)methyl]-1,3-propanediol, 26.2 g (0.1 mol) of triphenylphosphine, and 11 g (0.1 mol) of triethylamine. Monitor the reaction by thin-layer chromatography. Upon completion extract twice with 50 mL of 1N aqueous HCl. Add 1N NaOH to the aqueous portion until basic and extract twice with 100 mL of ether. Dry the organic phase over $Na_2SO_4$. Filter off the drying agent and evaporate the solvent in vacuo to obtain the title compound.

Preparation 22

1-Cyclohexylmethyl-3-[(4-nitrophenoxy)methyl]azetidine

In a manner similar to Preparation 2, react 1-cyclohexylmethyl-3-azetidinemethanol with 1-fluoro-4-nitrobenzene to obtain the title compound.

Preparation 23

4-[1-(Cyclohexylmethyl)azetidin-3-yl]methoxy]benzenamine

In a manner similar to Preparation 3, hydrogenate 1-cyclohexylmethyl-3-[(4-nitrophenoxy)methyl]azetidine to obtain the title compound.

Preparation 24

4-[Ethyl(heptyl)amino]-4-oxobutyric acid

In a manner similar to Preparation 4, react ethyl(heptyl)amine with succinic anhydride to obtain the title compound.

Preparation 25

4-[Ethyl(heptyl)amino]butanol

In a manner similar to Preparation 5, react 4-[ethyl(heptyl)amino]-4-oxobutyric acid with lithium aluminum hydride to obtain the title compound.

Preparation 26

N-Ethyl-N-[(4-nitrophenoxy)butyl]heptanamine

In a manner similar to Preparation 2, react 4-[ethyl(heptyl)amino]butanol with 4-fluoronitrobenzene to obtain the title compound.

Preparation 27

4-[4-(Ethyl(heptyl)amino]butoxy]benzenamine

In a manner similar to Preparation 3, hydrogenate N-ethyl-N-[(4-nitrophenoxy)butyl]heptanamine to obtain the title compound.

Preparation 28

1,2-Diethyl-4-piperidinone

To 100 mL of methylene chloride cooled to 0° C. is added 2-(trimethylsilyloxy)-1,3-butadiene (14.2 g, 0.1 mol), 8.5 g (0.1 mol) of N-ethyl-propanamine, and 14.2 g (0.1 mol) of borontrifluoride etherate. Monitor the reaction by thinlayer chromatography. Upon completion add 1N HCl until gas evolution ceases. Separate the aqueous layer and make it alkaline with 1N NaOH. Extract twice with 100 mL ether and dry over $Na_2SO_4$. Filter the drying agent and evaporated the solvent in vacuo to obtain the title compound.

Preparation 29

1,2-Diethyl-4-piperidinol

In a manner similar to Preparation 5, react 1,2-diethyl-4-piperidone with lithium aluminum hydride to obtain the title compound.

Preparation 30

1,2-Diethyl-4-(4-nitrophenoxy)piperidine

In a manner similar to Preparation 2, react 1,2-diethyl-4-piperidinol with 4-fluoronitrobenzene to obtain the title compound.

Preparation 31

4-[(1,2-Diethylpiperidin-4-yl)oxy]benzenamine

In a manner similar to Preparation 3, hydrogenate 1,2-diethyl-4-(4-nitrophenoxy)piperidine to obtain the title compound.

Preparation 32

3,4,5-Trimethoxybenzeneacetyl chloride

In a manner similar to Preparation 15, react 3,4,5-trimethoxybenzeneacetic acid with thionyl chloride to obtain the title compound.

Preparation 33

N-Methyl-3,4,5-trimethoxybenzeneacetamide

In a manner similar to Preparation 16, react 3,4,5-trimethoxybenzeneacetyl chloride with methylamine to obtain the title compound.

Preparation 34

N-Methyl-3,4,5-trimethoxybenzeneethanamine

In a manner similar to Preparation 5, react N-methyl-3,4,5-trimethoxybenzeneacetamide with lithium aluminum hydride to obtain the title compound.

Preparation 35

4-[[2-(3,4,5-Trimethoxyphenyl)ethyl](methyl)amino]-hexan-3-ol

Combine 22.5 g (0.1 mol) of N-methyl-3,4,5-trimethoxybenzeneethanamine and 10 g (0.1 mol) of 2,3-diethyloxirane in 150 mL of 90% aqueous methanol. Heat the reaction at 50° C. and follow the progress of the reaction by thin-layer chromatography. At the completion of the reaction remove the solvent in vacuo and chromatograph the residue on silica gel to obtain the title compound.

Preparation 36

N-[1-Ethyl-2-(4-nitrophenoxy)butyl]-N-methyl-3,4,5-trimethoxybenzeneethanamine

In a manner similar to Preparation 2, react 4-[[2-(3,4,5-trimethoxyphenyl)ethyl](methyl)amino]hexan-3-ol with 1-fluoro-4-nitrobenzene to obtain the title compound.

Preparation 37

N-[2-(4-Aminophenoxy)-1-ethylbutyl]-N-methyl-3,4,5-trimethoxybenzeneethanamine

In a manner similar to Preparation 3, hydrogenate N-[1-ethyl-2-(4-nitrophenoxy)butyl]-N-methyl-3,4,5-trimethoxybenzeneethanamine to obtain the title compound.

Preparation 38

Hexahydro-α-methyl-1H-azepine-1-propanol

In a manner similar to Preparation 1, react 3-chloro-1-butanol with hexahydro-1H-azepine to obtain the title compound.

Preparation 39

Hexahydro-1-[1-methyl-3-(4-nitrophenoxy)-propyl]-1H-azepine

In a manner similar to Preparation 2, react hexaydro-α-methyl-1H-azepine-1-propanol with 1-fluoro-4-nitrobenzene to obtain the title compound.

Preparation 40

4-[3-(Hexahydro-1H-azepin-1-yl)butoxy]-benzenamine

In a manner similar to Preparation 3, hydrogenate hexahydro-1-[1-methyl-3-(4-nitrophenoxy)propyl]-1H-azepine to obtain the title compound.

Preparation 41

N-[2-(Diethylamino)ethyl]-1,4-benzenediamine

In a manner similar to Preparation 3, hydrogenate N,N-diethyl-N'-(4-nitrophenyl)-1,2-ethanediamine to obtain the title compound.

Preparation 42

Hexahydro-1-(4-nitrophenyl)-4-propyl-1H-1,4-diazepine

In a manner similar to Preparation 2, react 1-fluoro-4-nitrobenzene with hexahydro-1-propyl-1H-1,4-diazepine to obtain the title compound.

Preparation 43

4-[Hexahydro-4-propyl-1H-1,4-diazepin-1-yl]benzenamine

In a manner similar to Preparation 3, hydrogenate hexahydro-1-(4-nitrophenyl)-4-propyl-1H-1,4-diazepine to obtain the title compound.

Preparation 44

3-(Morpholin-4-yl)-1-butanol

In a manner similar to Preparation 1, react 3-chloro-1-butanol with morpholine to obtain the title compound.

Preparation 45

3-(Morpholin-4-yl)-1-butanol methanesulfonate

To 100 mL of acetonitrile is added 15.9 g (0.1 mol) of 3-(morpholin-4-yl)-1-butanol and 18.4 g (0.1 mol) of methanesulfonic anhydride. Reflux the reaction and monitor by thin-layer chromatography. Upon completion remove the solvent in vacuo and add saturated aqueous sodium bicarbonate and methylene chloride. Dry the organic phase over $Na_2SO_4$. Filter off the drying agent and evaporate the solvent in vacuo to obtain the title compound.

Preparation 46

N-[3-(Morpholin-4-yl)butyl]-4-nitrobenzenamine

In a manner similar to Preparation 2, react 4-nitrobenzenamine with 3-(morpholin-4-yl)-1-butanol methanesulfonate to obtain the title compound.

Preparation 47

3,4-Dimethoxy-N-[3-(morpholin-4-yl)butyl]-N-(4-nitrophenyl)benzamide

In a manner similar to Preparation 16, react 3,4-dimethoxybenzoyl chloride with N-[3-(morpholin-4-yl)butyl]-4-nitrobenzenamine to obtain the title compound.

Preparation 48

N-(4-Aminophenyl)-3,4-dimethoxy-N-[3-(morpholin-4-yl)butyl]benzamide

In a manner similar to Preparation 3, hydrogenate 3,4-dimethoxy-N-[3-(morpholin-4-yl)butyl]-N-(4-nitrophenyl)-benzamide.

Preparation 49

N-[(3,4-Dimethoxyphenyl)methyl]-γ-methyl-N-(4-nitrophenyl)-4-morpholinepropanamine In a manner similar to Preparation 5, react N-(4-aminophenyl)-3,4-dimethoxy-N-[3-(morpholin-4-yl)butyl]-benzamide with lithium aluminum hydride to obtain the title compound.

Preparation 50

1-Ethoxy-3-(4-hexylpiperazin-1-yl)-2-propanol

To 100 mL of ethanol add 87 g (0.1 mol) of epichlorohydrin and zinc chloride (1 mL of a 0.872M solution in ether). Stir the reaction mixture at 100° C. for 2 days at which time remove the heat source and add 17.0 g (0.1 mol) of 1-hexyl-piperazine and 20 mL of 50% aqueous sodium hydroxide. Heat the reaction for 3 hours. Add 100 mL of water and extract twice with 200 mL of ether. Combine the organic layers and dry over $Na_2SO_4$. Remove the drying agent by filtration and evaporate the solvent in vacuo to obtain the title compound.

Preparation 51

1-(2-Chloro-3-ethoxypropyl)-4-hexylpiperazine

To 100 mL of chloroform is added 24 g (0.2 mol) of thionyl chloride and 27.2 g (0.1 mol) of 1-ethoxy-3-(4-hexylpiperazin-1-yl)-2-propanol. Reflux the reaction and monitor by thin-layer chromatography. Upon completion add saturated aqueous sodium bicarbonate until gas evolution ceases. Dry the organic phase over $Na_2SO_4$. Filter the drying agent and evaporate the solvent in vacuo to obtain the title compound.

Preparation 52

2-[Bis(phenylmethyl)amino]cyclohexanol methanesulfonic

In a manner similar to Preparation 45, react 2-[bis(-phenylmethyl)amino]cyclohexanol with methanesulfonic anhydride to obtain the title compound.

Preparation 53

2-[Bis(phenylmethyl)amino]cyclohexanecarbonitrile

To 100 mL of ether is added 10 g (0.2 mol) of sodium cyanide and 37.3 g (0.1 mol) of 2-[bis(phenylmethyl)amino]-cyclohexanol methanesulfonate. Reflux the reaction and monitor by thin-layer chromatography. Upon completion add 1N HCl until gas evolution ceases. Remove the solvent in vacuo and add saturated aqueous sodium bicarbonate and 100 mL methylene chloride. Dry the organic phase over $Na_2SO_4$. Filter off the drying agent and evaporate the solvent in vacuo to obtain the title compound.

Preparation 54

N-[2-(Aminomethyl)cyclohexyl]-N-phenylmethyl)-benzenemethanamine

In a manner similar to Preparation 5, react 2-[bis(-phenylmethyl)amino]cyclohexanenitrile with lithium aluminum hydride to obtain the title compound.

Preparation 55

N-[2-[(4-Nitrophenyl)aminomethyl]cyclohexyl]-N-(phenylmethyl)benzenemethanamine In a manner similar to Preparation 2, react 1-fluoro-4-nitrobenzene with N-[2-(aminomethyl)cyclohexyl]-N-(phenylmethyl)benzenemethanamine to obtain the title compound.

Preparation 56

N-[[2-[(Phenylmethyl)amino]cyclohexyl]methyl]-1,4-benzenediamine

In a manner similar to Preparation 3, hydrogenate N-[2-[(4-nitrophenyl)aminomethyl]cyclohexyl]-N-(phenylmethyl)benzenemethanamine to obtain the title compound.

Preparation 57

1-[(Cyclopropyl)methyl]-3-pyrrolidinemethanol

In a manner similar to Preparation 8, react cyclopropanecarboxaldehyde with 3-pyrrolidinemethanol to obtain the title compound.

Preparation 58

1-[(Cyclopropyl)methyl]-3-pyrrolidinemethanol methanesulfonate

In a manner similar to Preparation 45, react 1-cyclopropylmethyl-3-pyrrolidinemethanol with methanesulfonic anhydride to obtain the title compound.

Preparation 59

N-Ethyl-4-(1H-imidazol-1-yl)benzenamine

In a manner similar to Preparation 8, react 4-(1H-imidazol-1-yl)benzenamine with acetaldehyde to obtain the title compound.

Preparation 60

4-(1H-imidazol-1-yl)-N-(2-propenyl)benzenamine

In a manner similar to Example I react N-(2-propenyl)-1,4-benzenediamine with glyoxal, formaldehyde, and aqueous ammonia to obtain the title compound.

Preparation 61

3-Chloro-N-[4-(1H-imidazol-1-yl)phenyl]-N-(2-propenyl)-propanamide

In a manner similar to Preparation 16, react 3-chloroacetyl chloride with 4-(1H-imidazol-1-yl)-N-(2-propenyl)-benzenamine to obtain the title compound.

Preparation 62

3-(Dipropylamino)-N-[(4-1H-imidazol-1-yl)phenyl]-N-(2-propenyl)propanamide

In a manner similar to Preparation 4, react dipropylamine with 3-chloro-N-[4-(1H-imidazol-yl)phenyl]-N-(2-propenyl)propanamide to obtain the title compound.

Preparation 63

1-(-4-nitrophenyl)imidazole

In a manner similar to Preparation 1, react imidazole with 1-fluoro-4-nitrobenzene to obtain the title compound.

Preparation 64

4-(1H-Imidazol-1-yl)benzenamine

In a manner similar to Preparation 3, hydrogenate 1-(4-nitrophenyl)-1H-imidazole to obtain the title compound.

Preparation 65

1-Butyl-3-piperidinone

In a manner similar to Preparation 1, react 1-iodobutane with 3-piperidinone to obtain the title compound.

Preparation 66

1-Methyl-4-(4-nitrophenyl)piperazine

In a manner similar to Preparation 1, react 1-methylpiperazine with 1-fluoro-4-nitrobenzene to obtain the title compound.

Preparation 67

4-(4-Methylpiperazin-1-yl)benzenamine

In a manner similar to Preparation 3, hydrogenate 1-methyl-4-(4-nitrophenyl)piperazine over palladium on carbon in HCl/acetic acid to obtain the title compound.

Preparation 68

4-(1H-Imidazole-1-yl)-N-propylbenzenamine

In a manner similar to Preparation 8, react propanaldehyde with 4-(1H-imidazol-1-yl)benzenamine to obtain the title compound.

Preparation 69

2-[[[4-(1H-imidazol-1-yl)phenyl](propyl)amino]carbonyl]-cyclohexane carboxylic acid In a manner similar to Preparation 6, react 4-(1H-imidazol-1-yl)-N-propylbenzenamine with 1,2-cyclohexanedicarboxylic acid anhydride to obtain the title compound.

Preparation 70

2-[[[4-(1H-Imidazol-1-yl)phenyl](propyl)amino]carbonyl]-cyclohexane carbonyl chloride In a manner similar to Preparation 15, react 2-[[[4-(1H-imidazol-1-yl)phenyl](propyl)amino]carbonyl]cyclohexanecarboxylic acid with thionyl chloride to obtain the title compound.

Preparation 71

N,N-Diethyl-N'-[4-(1H-imidazol-1-yl)phenyl]-N'-propyl-1,2-cyclohexanedicarboxamide In a manner similar to Preparation 16, react diethylamine with 2-[[[4-(1H-imidazol-1-yl)phenyl](propyl)amino]-carbonyl]cyclohexanecarbonyl chloride to obtain the title compound.

Preparation 72

2-[4-(1H-Imidazol-1-yl)phenoxy]ethanamine dihydrochloride

To a cold solution of 11.3 g (0.235 mol) 50% sodium hydride in 50 mL dimethylformamide add 15 g (0.094 mol) 4-(1H-imidazol-1-yl)phenol portionwise. Maintain the temperature below 0° C. during the addition. After the addition, add dropwise a solution of 10.89 g (0.094 mol) 2-chloroethylamine hydrochloride in 50 mL dimethylformamide. After addition, warm the reaction mixture to 70° C., and heat for 24 hours. After this time, cool the reaction mixture and quench with water. Filter the solids and wash the mother liquors with 2X250 mL ether, 3X250 mL methylene chloride. Dry the methylene chloride layers over $Na_2SO_4$ and evaporate the solvents. Dissolve the resultant oil in methanolic HCl and evaporate the solvent to obtain the title compound.

NMR (DMSO-$d_6$): δ=3.22 (m,2), 4.30(t,2), 7.23(d,2), 7.76(d,2), 7.89(s,1), 8.23(s,1), 8.43(br s,4), and 9.65(s,1)ppm.

Preparation 73

1-Butyl-hexahydro-1H-azepine-3-carbonitrile

To 50 mL of acetonitrile is added 1 g (8.0 mmol) of hexahydro-1H-azepine-3-carbonitrile and 2.7 g (15 mmol) of iodobutane. Heat the reaction under reflux and monitor the reaction by thin-layer chromatography. Upon completion remove the solvent in vacuo and add 50 mL sat. sodium bicarbonate and 50 mL methylene chloride. Separate the organic layer and dry over $Na_2SO_4$. Filter off the drying agent and remove the solvent in vacuo to obtain the title compound.

Preparation 74

4-Fluorophenyl-(hexahydro-1-butyl-1H-azepin-3-yl)methanone

To 25 mL of dry ether under $N_2$ add 2 g (11 mmol) of 1-bromo-4-fluorobenzene and 0.25 g (0.10 mmol) of magnesium turnings. Initiate the reaction by standard procedures. When the magnesium filings are gone add 1 g (8.0 mmol) of 1-butyl-hexahydro-1H-azepine-3-carbonitrile and reflux the reaction mixture. Monitor the reaction by thin-layer chromatography. Upon completion add 50 mL 1M HCl and stir for one hr. The layers are separated and the aqueous layer is extracted with methylene chloride (25 mL). Add 4N NaOH to the aqueous layer until basic and extract with methylene chloride. Dry the organic phase over $Na_2SO_4$. Filter off the drying agent and evaporate the solvent in vacuo to obtain the title compound.

Preparation 75

2-(Dimethylamino)cyclohexanol methanesulfonate

To 100 mL of acetonitrile is added 14.3 g (0.1 mol) of 2-(dimethylamino)cyclohexanol and 18.4 g (0.1 mol) of methanesulfonic anhydride. Reflux the reaction and monitor by thin-layer chromatography. Upon completion remove the solvent in vacuo and add saturated aqueous sodium bicarbonate and methylene chloride. Dry the organic phase over $Na_2SO_4$. Filter off the drying agent and evaporate the solvent in vacuo to obtain the title compound.

Preparation 76

2-(Dimethylamino)cyclohexanecarbonitrile

To 200 mL of 80% aqueous ethanol add 10 g (0.2 mol) of sodium cyanide and 22.1 (0.1 mol) of 2-(dimethylamino)-cyclohexanol methanesulfonate. Reflux the reaction and monitor by thin-layer chromatography. Upon completion add in HCl until gas evolution ceases. Remove solvent in vacuo and add saturated aqueous sodium carbonate (ph=11) and 100 mL of methylene chloride. Separate the layers and dry the organic phase over $Na_2SO_4$. Filter the drying agent and evaporate the solvent in vacuo to obtain the title compound.

Preparation 77

[2-(Dimethylamino)cyclohexyl](4-fluorophenyl)methanone

In a manner similar to Preparation 74, react 2-(dimethylamino)cyclohexylcarbonitrile with 1-bromo-4-fluorobenzene to obtain the title compound.

Preparation 78

2-[[(Methylsulfonyl)oxy]methyl]cyclopropane carbonitrile

In a manner similar to Preparation 75, react 2-(hydroxymethyl)cyclopropanecarbonitrile with methanesulfonic anhydride and triethylamine to obtain the title compound.

Preparation 79

2-[(Diethylamino)methyl]cyclopropanecarbonitrile

To 10 mL of methanol add 1.75 g (2.10 mmol) of 2-[[(methylsulfonyl)oxy]methyl]cyclopropanecarbonitrile and 2.0 g (27 mmol) of diethylamine. Reflux the reaction and monitor by thin-layer chromatography. Upon completion remove the solvent in vacuo and add 50 mL methylene chloride and 50 mL sat. sodium carbonate. Separate the organic layer and dry over $Na_2SO_4$. Filter the drying agent and remove the solvent in vacuo to obtain the title compound.

Preparation 80

[2-[(Diethylamino)methyl]cyclopropyl](4-fluorophenyl)-methanone

In a manner similar to Preparation 74, react 2-[(diethylamino)methyl]cyclopropanecarbonitrile and 1-bromo-4-fluorobenzene to obtain the title compound.

Preparation 81

1-[2-(3,4-Dimethoxyphenyl)ethyl]azetidin-3-ol

In a manner similar to Preparation 73, react azetidin-3-ol with 1-bromo-2-(3,4-dimethoxyphenyl)ethane to obtain the title compound.

Preparation 82

1-[2-(3,4-Dimethoxyphenyl)ethyl]azetidin-3-ol methanesulfonate

In a manner similar to Preparation 75, react 1-[2-(3,4-dimethoxyphenyl)ethyl]azetidin-3-ol to obtain the title compound.

Preparation 83

1-[2-(3,4-Dimethoxyphenyl)ethyl]azetidine-3-carbonitrile

In a manner similar to Preparation 76, react 1-[2-(3,4-dimethoxyphenyl)ethyl]azetidin-3-ol methanesulfonate to obtain the title compound.

Preparation 84

[1-[2-(3,4-Dimethoxyphenyl)ethyl]azetidin-3-yl](4-fluorophenyl)methanone

In a manner similar to Preparation 74, react 1-[2-(3,4-dimethoxyphenyl)ethyl]azetidin-3-carbonitrile with 1-bromo-4-fluorobenzene to obtain the title compound.

Preparation 85

N-(2-Propenyl)cyclopentanemethanamine

To 100 mL of methanol is added 5.7 g (0.1 mol) of 2-propen-1-amine, 9.8 g (0.1 mol) of cyclopentanecarboxaldehyde and 12 g (0.2 mol) of sodium cyanoborohydride. Adjust the pH to 6 with concentrated HCl and monitor the reaction with thin-layer chromatography. Upon completion add concentrated HCl until gas evolution ceases. Add 300 mL of H$_2$O and extract once with 200 mL of ether. Add 1N NaOH to the aqueous solution until it is basic and extract twice with 200 mL of ether. Dry the organic phase over Na$_2$SO$_4$. Filter off the drying agent and remove the solvent in vacuo to obtain the title compound.

Preparation 86

5-[[(Cyclopentyl)methyl](2-propenyl)amino]hexanenitrile

In a manner similar to Preparation 85, react 5-oxohexanenitrile with N-(2-propenyl)cyclopentylmethanamine to obtain the title compound.

Preparation 87

5-[(Cyclopentylmethyl)(2-propenyl)amino]-1-(4-fluorophenyl)hexan-1-one

In a manner similar to Preparation 74, react 5-[(cyclopentylmethyl)(2-propenyl)amino]hexanenitrile with 1-bromo-4-fluorobenzene to obtain the title compound.

Preparation 88

4-(Diethylamino)-1-(4-fluorophenyl)-1-butanone

A suspension of 73.1 g (0.489 mol) 3-(diethylamino)propyl chloride and 11.87 g (0.489 mol) of magnesium in 300 mL of tetrahydrofuran is initiated with 0.25 mL of 3M ethylmagnesium bromide in diethyl ether and is refluxed overnight. After this time, the reaction is allowed to cool to 40° C. and is treated with 29.6 g (0.245 mol) of 4-fluorobenzonitrile. The initial exotherm is followed by applied heat and the reaction is refluxed for 3 hr. After this time, the reaction is allowd to cool to room temperature and is quenched with 250 mL of water. This mixture is extracted with 2×250 mL of methylene chloride. The combined organic layers are acidifed to pH=1 with 2N aq. hydrochloric acid and the resulting layers separated. The aqueous extract is washed with 100 mL of methylene chloride and is made basic with 4N of sodium hydroxide. The aqueous mixture is extracted with 3×300 mL of methylene chloride. The combined organic layers are dried over sodium sulfate, filtered and the solvent distilled in vacuo to provide crude title compound. This liquid is distilled under vacuum to provide the title compound.

NMR (CDCl$_3$): δ=1.04(t,6), 1.92(m,2), 2.52(m,6), 3.20(t,2), 7.14(t,2) and 8.02 (m,2)ppm.

Preparation 89

2-Bromo-1-[4-(1H-imidazol-1-yl)phenyl]ethanone hydrobromide

Add bromine (5.71 mL, 0.111 mol) to a solution of 4'-(1H-imidazol-1-yl)acetophenone (20.75 g, 0.111 mol) in 30–32% HBr in acetic acid. Stir the mixture overnight and collect the crystals. Wash the crystals with ethanol (3×50 mL) and air dry for 2h at room temperature to afford the title compound.

NMR (DMSO-d$_6$): δ=5.02(s,2), 7.95(s,1), 8.03(d,2), 8.26(d,2), 8.42(m,1), and 9.81 (s,1)ppm.

Preparation 90

α-(Bromomethyl)-4-(1H-imidazol-1-yl)benzenemethanol

Stir a mixture of 2-bromo-1-[4-(1H-imidazol-1-yl)phenyl]ethanone hydrobromide (15.45 g, 44.6 mmol) and sodium cyanoborohydride (5.61 g, 89.3 mmol) in methanol (250 mL). Add a crystal of methyl orange and adjust the pH to 3.0 with 1.35M hydrochloric acid in methanol. Maintain the pH at 3.0 for about 2 hr. Treat the resulting solution with decolorizing carbon and filter through celite. Concentrate the filtrate and add water (200 mL) and methylene chloride (100 mL) to the residue. Adjust the pH to 7.5 with 2N NaOH solution. Separate the layers and extract the aqueous layer with methylene chloride (100 mL) and combine, dry over Na$_2$SO$_4$, filter and concentrate in vacuo. Add ethyl acetate to the residue to afford crystals of the title compound.

NMR (CDCl$_3$): δ=2.88(br s,1), 3.56(dd,1), 3.68(dd,1), 5.00(dd,1), 7.22(s,1), 7.29(s,1), 7.42(d,2), 7.53(d,2), and 7.85(s,1) ppm.

Preparation 91

N-[2-(4-Methylphenoxy)ethyl]acetamide

Combine 5.0 g (0.046 mol) 4-methylphenol and 3.9 g (0.46 mol) 2-methyl-2-oxazoline under a nitrogen atmosphere and heat to 175° C. for 18 hours. After this time, cool the reaction mixture and add 50 mL of methylene chloride. Wash the organics with 3×10 mL of 10% potassium hydroxide, dry over sodium sulfate and remove the solvents to obtain the title compound.

Preparation 92

N-Ethyl-N-[2-(4-methylphenoxy)ethyl]amine

To a chilled suspension of 0.49 g (013 mol) lithium aluminium hydride in 50 mL anhydrous ether, add 5.0 g (025 mol) N-[2-(4-methylphenoxy)ethyl]acetamide at a rate which maintains the reaction temperature below 10° C. Allow to warm to room temperature and stir at ambient temp. for 24 hrs. After this time, quench the mixture with H₂O and filter the salts. Concentrate the filtrate to obtain the title compound.

Preparation 93

N-Ethyl-N-(2-hydroxyethyl)-N-[2-(4-methylphenoxy)ethyl]-amine

Add 0.90 g (011 mol) 2-chloroethanol to a solution of 2.0 g (0.11 mol) N-ethyl-N-[2-(4-methylphenoxy)ethyl]amine and 1.7 g (012 mol) potassium carbonate in 50 mL methanol. Stir at room temperature for 24 hr. After this time, remove the solvents in vacuo and dissolve the residue in 25 mL water. Adjust the aqueous to pH=8 with 5% sodium bicarbonate solution and extract 3×50 mL methylene chloride. Dry the combined organics over sodium sulfate and evaporate the solvent to obtain the desired product.

Preparation 94

N-(2-Chloroethyl)-N-ethyl-N-[2-(4-(methylphenoxy)ethyl)]-amine hydrochloride

Combine 2.0 g (8.96 mmol) N-ethyl-N-(2-hydroxyethyl)-N-[2-(4-methylphenoxy)ethyl]amine and 10 mL thionyl chloride and heat to reflux for 24 hr. After this time, distill off the excess thionyl chloride to obtain the desired product.

Preparation 95

2-[3-Chlorophenoxy]ethylamine

Add 5.0 g (38.9 mmol) of 3-chlorophenol to a 0° C. suspension of 3.42 g (85.6 mmol, 2.2 eq., 60% by wt. in mineral oil) of sodium hydride in 100 mL of dry tetrahydrofuran. Once the 3-chlorophenol is dissolved add 9.93 g (85.6 mmol, 2.2 eq.) of 2-chloroethylamine hydrochloride and stir at room temperature for 17 hr. Concentrate the reaction mixture and partition between 200 mL of methylene chloride and 50 mL water. Dry the organic layer over Na₂SO₄ and concentrate in vacuo to obtain the title compound.

Preparation 96

2-(2-Trifluoromethylphenoxy)ethylamine

Add 5.0 g (30.9 mmol) of 2-trifluoromethylphenol to a 0° C. suspension of 2.72 g (67.9 mmol, 2.2 eq, 60% by wt. in mineral oil) of sodium hydride in 100 mL of dry tetrahydrofuran. Once the 2-trifluoromethylphenol is dissolved add 7.88 g (67.9 mmol, 2.2 eq) of 2-chloroethylamine hydrochloride and stir at room temperature for 18 hr. Concentrate the reaction mixture and partition between 200 mL of methylene chloride and 50 mL water. Dry the organic layer over Na₂SO₄ and concentrate in vacuo to obtain the title compound.

EXAMPLES

Example 1

1-[4-[1-Methyl-3-(morpholin-4-yl)propoxy]phenyl]-1H-imidazole

A mixture of 25.4 g (0.1 mol) of 4-[1-methyl-3-(morpholin-4-yl)propoxy]benzenamine, 6.8 g of 25% aqueous ammonia, and 10 mL of 2-propanol, and a mixture of 5.8 (0.1 mol) of glyoxal and 7.5 (0.1 mol) of 40% aqueous formaldehyde are simultaneously added into 20 mL of 1-propanol in the course of 30 minutes at 80° C. Monitor the reaction by thin-layer chromatography. Upon completion remove the solvent in vacuo to obtain the title compound.

Example 2

1-[4-[[2-[[4-Pentylpiperazin-1-yl]methyl]cyclopropyl]methoxy]phenyl]-1H-imidazole In a manner similar to Example 1, react 4-[[2-[[4-pentylpiperazin-1-yl]methyl]cyclopropyl]methoxy]benzeneamine, aqueous ammonia, aqueous formaldehyde and aqueous glyoxal to obtain the title compound.

Example 3

N-heptyl-3-[[4-1H-imidazol-1-yl)phenoxy]methyl]-N-2-propenyl cycloheptanamine

In a manner similar to Example 1, react 3-[[4-aminophenoxy]methyl]-N-heptyl-N-(2-propenyl)cycloheptanamine with aqueous formaldehyde, aqueous ammonia and aqueous glyoxal to obtain the title compound.

Example 4

1-[2-(4-Chlorophenyl)ethyl]-4-[[4-(1H-imidazol-1-yl)phenoxy]methyl]piperidine

In a manner similar to Example 1, react formaldehyde, glyoxal, aqueous ammonia and 4-[[1-[2-(4-chlorophenyl)-ethyl]piperidin-4-yl]methoxy]benzenamine to obtain the title compound.

Example 5

1-[4-[[1-(cyclohexylmethyl)azetidin-3-yl]methoxy]-phenyl]-1H-imidazole

In a manner similar to Example 1, react 4-[1-(cyclohexylmethyl) azetidin-3-yl]methoxy]benzenamine with aqueous ammonia, aqueous formaldehyde and glyoxal to obtain the title compound.

Example 6

2-[4-(1H-Imidazol-1-yl)phenoxy]-N,N-bis(phenylmethyl)-ethanamine dihydrochloride To a cold suspension of 33 g (0.82 mol) 50% sodium hydride in 500 mL dimethylformamide, add 50.4 g (0.315 mol) 4-(1H-imidazol-1-yl)phenol portionwise, maintaining the temp below 10° C. After addition, stir at room temp for 1 hr. Add 93.2 (0.315 mol) 2-chloro-N,N-dibenzylethanamine hydrochloride portionwise followed by 2.35 g (0.16 mol) sodium iodide. Heat the reaction to 50° C. for 24 hr. After this time, quench with 15 mL H₂O, filter, and remove the solvents. Dissolve the residue in methanolic HCl and remove the solvents to provide the title compound which can be recrystallized from isopropanol.

| | |
|---|---|
| NMR (DMSO-d₆): δ = 100° C. | 3.17(t,2), 4.09(S,4), 4.33(t,2), 7.09(d,2), 7.35(m,5), 7.53(m,5), 7.63(d,3), 7.97(s,1) and 9.22(s,1) ppm. |

Example 7

N-Ethyl-N-[4-[4-(1H-imidazol-1-yl)phenoxy]butyl]-heptanamine

In a manner similar to Example 1, react 4-[4-[ethyl(heptyl)amino]butoxy]benzenamine, aqueous formaldehyde, aqueous ammonia and glyoxal to obtain the title compound.

Example 8

1,2-Diethyl-4-[4-[1H-imidazol-1-yl]phenoxy]piperidine

In a manner similar to Example 1, react 4-(1,2-diethylpiperidin-4-oxy)benzenamine with aqueous formaldehyde, aqueous ammonia and glyoxal to obtain the title compound.

Example 9

N-[2-[4-(1H-Imidazol-1-yl)phenoxy]-1-ethylbutyl]-N-methyl-3,4,5-trimethoxybenzeneethanamine In a manner similar to Example 1, react formaldehyde, glyoxal, aqueous ammonia and N-[2-(4-aminophenoxy)-1-ethylbutyl]-N-methyl-3,4,5-trimethoxybenzeneethanamine to obtain the title compound.

Example 10

Hexahydro-1-[3-[4-(1H-imidazol-1-yl)phenoxy]-1-methylpropyl]-1H-azepine

In a manner similar to Example 1, react 3-[3-(hexahydro-1H-azepin-1-yl)butoxy]benzenamine with aqueous formaldehyde, aqueous ammonia and glyoxal to obtain the title compound.

Example 11

N,N-Diethyl-N'-[4-(1H-imidazol-1-yl)phenyl]-1,2-ethanediamine

In a manner similar to Example 1, react aqueous formaldehyde, aqueous ammonia, glyoxal and N'-(4-aminophenyl)-N,N-diethyl-1,2ethanediamine to obtain the title compound.

Example 12

Hexahydro-1-[4(1H-imidazol-1-yl)phenyl]-4-propyl-1H-1,4-diazepine

In a manner similar to Example 1, react 4-(hexahydro-4-propyl-1H-1,4-diazepin-1-yl)benzenamine with formaldehyde, aqueous ammonia and glyoxal to obtain the title compound.

Example 13

N-[(3,4-dimethoxyphenyl)methyl]-4-(1H-imidazol-1-yl)-N-[3-(morpholin-4-yl)butyl]benzenamine In a manner similar to Example 1, react aqueous formaldehyde, glyoxal, aqueous ammonia and N-[3-(morpholin-4-yl)butyl]-N-[(3,4-dimethoxyphenyl)methyl]-1,4-benzenediamine to obtain the title compound.

Example 14

β-[(Ethoxy)methyl]-4-hexyl-N-[4-(1H-imidazol-1-yl)phenyl]-N-methyl-1-piperazineethanamine In a manner similar to Preparation 2, react 4-(1H-imidazol-1-yl)-N-methylbenzenamine with 1-(2-chloro-3-ethoxypropyl)-4-hexylpiperazine to obtain the title compound.

Example 15

N-[4-(1H-Imidazol-1-yl)phenyl]-2-[bis(phenylmethyl)amino]cyclohexanemethanamine

In a manner similar to Example 1, react formaldehyde, glyoxal, aqueous ammonia and N-[[2-[bis(phenylmethyl)-amino]cyclohexyl]methyl]-1,4-benzenediamine to obtain the title compound.

Example 16

N-[4-(1H-imidazol-1-yl)phenyl]-2-[(phenylmethyl)amino]-cyclohexanemethanamine

In a manner similar to Preparation 3, hydrogenate N-[4-(1H-imidazol-1-yl)phenyl]-2-[bis(phenylmethyl)amino]-cyclohexanemethanamine to obtain the title compound.

Example 17

1-[(Cyclopropyl)methyl]-N-ethyl-N-[4-(1H-imidazol-1-yl)-phenyl]-3-pyrrolidinemethanamine In a manner similar to Preparation 2, react 1-cyclopropylmethyl-3-pyrrolidinemethanol methanesulfonate with N-ethyl-4-(1H-imidazol-1-yl)benzenamine to obtain the title compound.

Example 18

N,N-Dipropyl-N'-[4-(1H-imidazol-1-yl)phenyl]-N'-(2-propenyl)-1,3-propanediamine

In a manner similar to Preparation 4, react 3-(dipropylamino)-N-[4-(1H-imidazol-1-yl)phenyl]-N-(2-propenyl)propanamide with lithium aluminum hydride to obtain the title compound.

Example 19

1-Butyl-N-[4-(1H-imidazol-1-yl)-2-methylphenyl]-3-piperidinamine

In a manner similar to Preparation 8, react 1-butyl-3-piperidinone with 4-(1H-imidazol-1-yl)-2-methylbenzenamine and sodium cyanoborohydride to obtain the title compound.

Example 20

1-[4-(1H-imidazol-1-yl)phenyl]-4-methylpiperazine

In a manner similar to Example 1, react formaldehyde, glyoxal, aqueous ammonia and 4-(4-methylpiperazin-1-yl)-benzenamine to obtain the title compound.

Example 21

N,N-diethyl-N'-[4-(1H-imidazol-1-yl)phenyl]-N'-propyl-1,2-cyclohexanedimethanamine In a manner similar to Preparation 4, react N,N-diethyl-N'-[4-(1H-imidazol-1-yl)phenyl]-N'-propyl-1,2-cyclohexanedicarboxamide to obtain the title compound.

Example 22

1-[4-[[3-(2-methylpropoxy)-2-pyrrolidin-1-yl]propoxy]-phenyl]-1H-imidazole

In a manner similar to Example 6, react 4-(1H-imidazol-1-yl)phenol with 1-[2-chloro-3-(2-methylpropoxy)-propyl]pyrrolidine to obtain the title compound.

Example 23

2-[4-(1H-imidazol-1-yl)phenoxy]-N-(phenylmethyl)-ethanamine

To a chilled suspension of 39.5 g (0.823 mol) 50% sodium hydride in 500 mL dimethylformamide add 37.32 g (0.233 mol) 4-(1H imidazol-1-yl)phenol. When the addition is complete, stir the reaction mixture at room temperature until gas evolution ceases. After this time, chill the reaction mixture below 0° C. and slowly add 60.22 g (0.292 mol) N-benzyl(2-chloro)ethylamine hydrochloride. When the addition is complete, heat the reaction mixture to 65° C. Follow the progress of the reaction by thin-layer chromatography on silica gel (methylene chloride:methanol) (9:1). At the completion of the reaction, add 20 mL water to the cooled mixture. Filter the slats and remove the solvents in vacuo to obtain an oil. Column chromatograph the oil on silica gel using methylene chloride+methanol (1+99→1+19) as eluent. Collect the appropriate fractions and remove the solvents to obtain the title compound as the free base. Dissolve the free base in excess methanolic HCl solution and remove the solvent in vacuo to provide the title compound.

NMR (DMSO-$d_6$): $\delta$=3.32(br s,3), 4.24(s,2), 4.42(t,2), 7.22(d,2), 7.43(m,3), 7.63(m,2), 7.76(m,3), 8.15(s,1), 9.47(s,1) and 9.81(br s,2)ppm.

Example 24

N,N-Diethyl-2-[4-(1H-imidazol-1-yl)phenoxy]ethanamine

Dissolve 4-(1H-imidazol-1-yl)phenol (4.02 g, 25.1 mmol) in methanol (100 mL) containing potassium hydroxide (3.52 g, 62.74 mmol). Add 2-diethylaminoethyl chloride hydrochloride to this mixture and heat to reflux under nitrogen overnight. Cool the mixture and concentrate in vacuo. Dissolve the residue in water (50mL) and adjust the pH to 13 with 1N NaOH solution. Wash with 2×100 mL of methylene chloride, combine, dry ($Na_2SO_4$) and concentrate in vacuo. This residue is dissolved in ethanol and 37% hydrochloric acid is added until pH=1.0. Concentration affords crystals which are recrystallized from isopropanol/ethanol (ca. 4+1). Drying at 80° C. for 5 hr at 1.0 mm give the title compound.

NMR (DMSO-$d_6$): $\delta$=1.28(t,6), 3.22(m,4), 3.51(m,2), 4.53(t,2), 7.25(d,2), 7.80(d,2), 7.91(m,1), 8.26(m,1), 9.73(s,1) and 11.30(s,1)ppm.

Example 25

N-[2-[4-(1H-imidazol-1-yl)phenoxy]ethyl]octan-3-amine

In a manner similar to Preparation 8, react 2-[4-(1H-imidazol-1-yl)phenoxy]ethanamine with 3-octanone and sodium cyanoborohydride in methanol to obtain the title compound.

Example 26

1-Butyl-hexahydro-1H-azepin-3-yl)[4-(1H-imidazol-1-yl)phenol]methanone

To 3 mL of dimethylsulfoxide is added 1.0 g (4.5 mmol) of (4-fluorophenyl)(hexahydro-1-butyl-1H-azepin-3-yl)-methanone, 0.5 g (6.8 mmol) of 1H-imidazole, and 1.2 g (8.6 mmol) of potassium carbonate. Heat the reaction at 150° C. and monitor by thin-layer chromatography. Upon completion add 50 mL water and 50 mL methlene chloride. Separate the layers and dry the organic layer over $Na_2SO_4$. Filter off the drying agent and evaporate the solvent in vacuo to obtain the title compound.

Example 27

1-Butyl-hexahydro--[4-(1H-imidazol-1-yl)-phenyl]-1H-azepine-3-methanol

To 20 mL of methanol add 1.0 g (3.1 mmol) of 1-butylhexahydro-1H-azepin-3-yl)[4-(1H-imidazol-1-yl)phenyl]-methanone and 0.2 g (5 mmol) of sodium borohydride. Monitor the reaction by thin-layer chromatography. Upon completion add concentrated HCl until gas evolution ceases. Add 1N NaOH until basic and extract twice with 50 mL of methylene chloride. Combine the organic layers and dry over $Na_2SO_4$. Filter off the drying agent and evaporate the solvent in vacuo to obtain the title compound.

Example 28

1-Butyl-hexahydro-3-[4-(1H-imidazol-1-yl)-phenylmethyl]-1H-azepine

To 2 mL of diethylene glycol is added 0.5 g (9 mmol) of potassium hydroxide and the mixture is heated until it is homogeneous. Remove the heat and add 1.0 g (3.1 mmol) of 1-butyl-hexahydro-1H-azepin-3-yl)[4-(1H-imidazol-1-yl)-phenyl]methanone and 0.45 g (7.8 mmol) of 85% hydrazine hydrate. Heat the reaction under reflux and monitor by thin-layer chromatography. Upon completion add 50 mL water and 50 mL methylene chloride. Separate the layers and dry the organic layer over $Na_2SO_4$. Filter off the drying agent and evaporate the solvent in vacuo to obtain the title compound.

Examle 29

[2-(Dimethylamino)cyclohexyl][4-(1H-imidazol-1-yl)-phenyl]methanone

In a manner similar to Example 26, react [2-dimethylamino)cyclohexyl](4-fluorophenyl)methanone with 1H-imidazole to obtain the title compound.

Example 30

$\alpha$-[2-Dimethylamino)cyclohexyl]-4-(1H-imidazol-1-yl)-benzenemethanol

In a manner similar to Example 27, react [2-(dimethylamino)cyclohexyl][4-(1H-imidazol-1-yl)phenyl]methanone with sodium borohydride to obtain the title compound.

Example 31

N,N-Dimethyl-2-[4-(1H-imidazol-1-yl)phenylmethyl]-cyclohexanamine

In a manner similar to Example 28, react [2-(dimethylamino)cyclohexyl][4-(1H-imidazol-1-yl)phenyl]methanone with potassium hydroxide and hydrazine in diethylene glycol to obtain the title compound.

Example 32

[2-[(Diethylamino)methyl]cyclopropyl][4-(1H-imidazol-1-yl-phenyl]methanone

In a manner similar to Example 26, react [2-[(diethylamino)methyl]cyclopropyl](4-fluorophenyl)methanone with 1H-imidazole to obtain the title compound.

Example 33

α-[2-[(Diethylamino)methyl]cyclopropyl]-4-(1H-imidazol-1-yl)benzenemethanol

In a manner similar to Example 27, react [2-[(diethylamino)methyl]cyclopropyl][4-(1H-imidazol-1-yl)phenyl]-methanone with sodium borohydride to obtain the title compound.

Example 34

N,N-Diethyl-2-[[4-(1H-imidazol-1-yl)phenyl]methyl]-cyclopropanemethanamine

In a manner similar to Example 28, react [2-[(diethylamino)methyl]cyclopropyl][4-(1H-imidazol-1-yl)phenyl]-methanone with potassium hydroxide and hydrazine in diethylene glycol to obtain the title compound.

Example 35

[1-[2-(3,4-Dimethoxyphenyl)ethyl]azetidin-3-yl][4-(1H-imidazol-1-yl)phenyl]methanone In a manner similar to Example 26, react [1-[2-(3,4-dimethoxyphenyl)ethyl]azetidin-3-yl](4-fluorophenyl)-methanone with 1H-imidazole to obtain the title compound.

Example 36

1-[2-(3,4-Dimethoxyphenyl)ethyl]-α-[4-(1H-imidazol-1-yl)-phenyl]azetidine-3-methanol In a manner similar to Example 27, react [1-[2-(3,4-dimethoxyphenyl)ethyl]azetidin-3-yl][4-(1H-imidazol-yl)phenyl]methanone with sodium borohydride to obtain the title compound.

Example 37

1-[4-[[1-[2-(3,4-Dimethoxyphenyl)ethyl]azetidin-3-yl]-methyl]phenyl]imidazole

In a manner similar to Example 28, react [1-[2-(3,4-dimethoxyphenyl)ethyl]azetidin-3-yl][4-(1H-imidazol-1-yl)-phenyl]methanone with potassium hydroxide and hydrazine in diethylene glycol to obtain the title compound.

Example 38

5-[(Cyclopentylmethyl)(2-propenyl)amino]-1-[4-(1H-imidazol-1-yl)phenyl]hexan-1-one In a manner similar to Example 26, react 5-[(cyclopentylmethyl)(2-propenyl)amino]-1-(4-fluorophenyl)hexan-1-one with 1H-imidazole to obtain the title compound.

Example 39

α-[4-[(Cyclopentylmethyl)(2-propenyl)amino]pentyl]-4-(1H-imidazol-1-yl)benzenemethanol In a manner similar to Example 27, react 5-[(cyclopentylmethyl)(2-propenyl)amino]-1-[4-(1H-imidazol-1-yl)-phenyl]hexan-1-one with sodium borohydride to obtain the title compound.

Example 40

N-(Cyclopentylmethyl)-4-(1H-imidazol-1-yl)-α-methyl-N-(2-propenyl)benzenepentanamine In a manner similar to Example 28, react 5-[(cyclopentylmethyl)(2-propenyl)amino]-1-[4-(1H-imidazol-1-yl)-phenyl]hexan-1-one with potassium hydroxide and hydrazine in diethylene glycol to obtain the title compound.

Example 41

4-(Diethylamino)-1-[4-(1H-imidazol-1-yl)phenyl]butanone dihydrochloride hydrate

A mixture of 50.0 g (0.211 mol) 4-(diethylamino)-1-(4-fluorophenyl)butanone, 29.0 g (0.42 mol) imidazole, 58.24 g (0.42 mol) anhydrous potassium carbonate and 50 mL dimethylsulfoxide is heated to 150° C. for 18 hr and to 165° C. for 3 hr. After this time, the mixture is treated with 500 mL H$_2$O and is extracted with 2×400 mL methylene chloride. The organic layers are washed with 5×300 mL water. The organic layer is dried over sodium sulfate, filtered and the solvent evaporated to provide crude title compound as free base. This material is dissolved in 200 mL methanol, acidified to pH=1 with hydrochloric acid (gas) and the solvent removed in vacuo. The residue is recrystallized from methanol-isopropanol ($\frac{2}{3}$) to provide the title compound.

NMR (DMSO-d$_6$) δ=1.27(t,6), 2.03(m,2), 2.1–5.2(br 1,), 3.12(m,6), 3.30(t,2), 7.94(s,1), 8.04(d,2), 8.21(d,2), 8.43(s,1), 9.89(s,1) and 10.9(br s,1)ppm.

Example 42

1-[4-(1H-Imidazol-1-yl)phenyl]-4-[4-methylpiperidin-1-yl]-butanone dihydrochloride hydrate In a manner similar to Example 26, react 1-(4-fluorophenyl)-4-(4-methylpiperidin-1-yl)-1-butanone with imidazole in dimethylsulfoxide with potassium carbonate to obtain the title compound.

NMR (DMSO-d$_6$): δ=0.86–1.06(m,3), 1.42–1.95(m,5), 2.0–2.18(m,2), 2.5–5.5(br,1), 2.70–2.90(m,2), 3.0–3.24(m,2), 3.80(t,2), 3.44(d,2), 7.92(s,1), 8.04(d,2), 8.24(d,2), 8.43(s,1), 9.90(s,1) and 10.87(br,1)ppm.

Example 43

4-(1H-Imidazol-1-yl)-α-[((1-methylethyl)amino)methyl]-benzenemethanol sulfuric acid salt (1:1) hemihydrate Add α-(bromomethyl-4-(1H-imidazol-1-yl)benzenemethanol (6.20 g, 23.2 mmol) to a 0° C. solution of isopropylamine (40 mL) in methanol (20 mL). Stir the resultant mixture at room temperature overnight. Concentrate the mixture in vacuo and chromatograph the residue on alumina (neutral, activity III, 250 g) using 2% methanol in methylene chloride as eluent. Collect the product fractions and concentrate in vacuo. Dissolve the product in ethanol and add 1 equivalent of sulfuric acid to obtain crystals. Dry the crystals at 80° C. for 1.5 hr at p=10 mm to obtain the title compound.

NMR (DMSO-d$_6$): δ=1.22(t,6), 3.01(dd,1), 3.14(dd,1), 3.40(m,1), 4.92(dd,1), 6.20 (br s,1), 7.11(s,1), 7.55(d,2), 7.68(d,2), 7.75(s,1), 8.28(s,1), and ca. 8.50(br s,3)ppm.

Example 44

α-[[Ethyl(phenylmethyl)amino]methyl]-4-(1H-imidazol-1-yl)-benzenemethanol phosphoric acid salt Add α-(bromomethyl-4-(1H-imidazol-1-yl)benzenemethanol (7.80 g, 29.2 mmol) to a room temperature solution of N-ethylbenzylamine (21.7 mL, 146.0 mmol) in tetrahydrofuran (75 mL). Reflux the resultant mixture for about 5.5 days. Cool to room temperature and concentrate in vacuo. Chromatograph the resultnat residue on alumina (neutral, activity III, 500 g) using first methylene chloride then 2.5% methanol in methylene chloride as eluent. Collect the product fractions and concentrate in vacuo. The residue is dissolved in ethanol and phosphoric acid added until the pH is 2.5. Concentration in vacuo affords the title compound.

NMR (D₂O/TSP): δ=1.43(t,3), 3.44(m,4), 4.49(m,2), 5.10(br s,1), 7.41-7.85(m,11), and 9.06(s,1; exchangeable with D₂O) ppm. EtOH at 1.16 and 3.65 ppm.

Example 45

α-[4-(1H-Imidazol-1-yl)phenyl-4-methyl-1-piperidine ethanol

Add α-(bromomethyl)-4-(1H-imidazol-1-yl)benzenemethanol (8.88 g, 33.24 mmol) to a room temperature solution of 4-methylpiperidine (11.8 mL, 99.73 mmol) in tetrahydrofuran (90mL). Stir the resultant mixture for 2.5 days and concentrate in vacuo. Chromatograph the residue on alumina (neutral, activity III, 100 g) using first methylene chloride than 2% methanol in methylene chloride as eluent. Collect the product fraction and concentrate in vacuo to give a solid. Recrystallize the solid from petroleum ether/ethyl acetate (ca. 4+1). Drying at 50° C. for 2 hr at p=1.0 mm affords the title compound.

NMR (CDCl₃): δ=0.95(d,3), 1.20-1.45(m,3), 1.60-1.75(m,2), 2.04(dt,1), 2.27-2.45(m,2), 2.52(dd,1), 2.77(br d,1), 3.12(br d,1), 4.36(br s,1), 4.76(dd,1), 7.20(s,1), 7.27(s,1), 7.36(d,2), 7.48(d,2), and 7.84(s,1)ppm.

Example 46

N,N-Diethyl-4-(1H-imidazol-1-yl)benzenemethanamine dihydrochloride 4-(1H-Imidazol-1-yl)benzenemethanol (71.8 mmol) is stirred in Ch₂Cl₂ (150 mL) at 0° C. under a nitrogen atmosphere. Pyridine (86.5 mmol) and methanesulfonyl chloride (80.1 mmol) are added to the solution. The mixture is stirred for 10 minutes at 0° C. and warmed to room temperature with continued stirring overnight. Diethylamine (0.24 mol) is added to the mesylate and stirring is continued overnight. The reaction mixture is stripped under reduced pressure and the residue is partitioned between H₂O and methylene chloride. The aqueous portion is extracted with methylene chloride, and the combined organic portions are washed with brine and dried with Na₂SO₄. Removal of the solvent under reduced pressure yields the product as an oil. The hydrochloride salt is formed in and recrystallized from acetonitrile/methanol to yield the title compound.

NMR(DMSO-d₆): δ=1.27(t,6), 2.95-3.13(m,4), 3.20-3.60(br s,1+H₂O), 4.35(d,2), 7.85(s,1), 7.88-7.96(m,4), 8.28(s,1), 9.60(s,1), and 10.85-10.94(br s,1) ppm.

Example 47

4-(1H-Imidazol-1-yl)-α-[[2-(3-chlorophenoxy)ethyl]amino]-methyl]benzenemethanol sulfuric acid salt In a manner similar to Example 43, react α-(bromomethyl)-4-(1H-imidazol-1-yl)benzenemethanol with 2-(3-chlorophenoxy)ethylamine to obtain the title compound.

Example 48

N-Ethyl-N-[2-(4-methylphenoxy)ethyl]-2-[4-(1H-imidazol-1-yl)-phenoxy]ethanamine dihydrochloride In a manner similar to Example 24, react 4-(1H-imidazol-1-yl)phenol with N-(2-chloroethyl)-N-ethyl-[2-(4-methylphenoxy)ethylamine hydrochloride to obtain the title compound.

Example 49

4-(1H-Imidazol-1-yl)-N-[2-(2-trifluorophenoxy)ethyl]-benzenmethanamine dihydrochloride In a manner similar to example 46, react 4-(1H-imidazol-1-yl)benzenemethanol with methanesulfonyl chloride and react this intermediate mesylate with, 2-(2-trifluoromethylphenoxy)ethylamine to obtain the title compound.

We claim:

1. A compound of the following formula I:

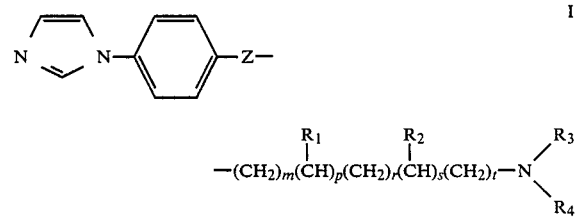

wherein Z is —CH₂—,

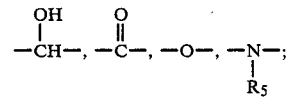

m,p,r,s,t are the integers 0,1;

R₁ is hydrogen, lower alkyl, or collectively with R₂ is an alkylene chain to form a saturated carbocyclic ring of from 3 to 7 ring atoms, or collectively with R₃ is an alkylene chain to form a heterocyclic ring of from 4 to 7 ring atoms;

R₂ is hydrogen, lower alkyl, loweralkoxyloweralkyl;

R₃ is 2-propenyl, C₁-C₈ straight or branched chain alkyl, cycloalkyl, cycloalkyl(lower)alkyl, phenylalkyl, phenoxyalkyl, substituted phenylalkyl, substituted phenoxyalkyl, or collectively with R₄ forms a saturated heterocyclic ring of from 4 to 7 ring atoms which may be substituted by one or more methyl groups, or collectively with R₄ forms the system —CH₂CH₂—O—CH₂—CH₂— or

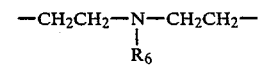

or collectively with R₅ is an alkylene chain to form a piperazine or a hexahydro 1,4-diazepine ring system;

R₄ is hydrogen, 2-propenyl, C₁-C₈ straight or branched chain alkyl, cycloalkyl, cycloalkyl(lower)alkyl, phenylalkyl, substituted phenylalkyl;

R₅ is hydrogen, C₁-C₈ straight or branched chain alkyl, 2-propenyl, cycloalkyl, cycloalkyl(lower)alkyl, phenylalkyl, substituted phenylalkyl;

$R_6$ is hydrogen, $C_1$-$C_8$ straight or branched chain alkyl, 2-propenyl, cycloalkyl, cycloalkyl(lower)alkyl, phenylalkyl, substituted phenylalkyl; with the provisos that, (a) when $R_1$ and $R_2$ collectively form a ring then $R_3$ cannot collectively form a ring with $R_5$, (b) when Z is —$CH_2$— then $R_1$ and $R_2$ cannot be hydrogen or lower alkyl, $R_4$ cannot be hydrogen and $R_3$ and $R_4$ cannot be $C_1$-$C_8$ straight or branched chain alkyl.

(c) when Z is —O— or

then the sum of m,p,r,s, and t must be at least 2, and (d) when Z is

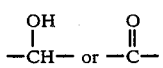

then the sum of m,p,r,s, and t must be at least 1.

2. A compound of claim 1 wherein Z is —O—.

3. A compound of claim 1 wherein Z is

4. A compound of claim 1 wherein the sum of m+p+r+s+t is 2.

5. A compound of claim 1 wherein m,r and t are O and $R_1$ collectively with $R_2$ is an alkylene chain to form a saturated carbocyclic ring of 6 ring atoms.

6. A compound of claim 2 which is N,N-diethyl-2-[4-(1H-imidazol-1-yl)phenoxy]ethanamine.

7. A compound of claim 2 which is 2-[4-(1H-imidazol-1-yl)-phenoxy]-N,N-bis(phenylmethyl)ethanamine.

8. A compound of claim 2 which is 2-[4-(1H-imidazol-1-yl)-phenoxy]-N-(phenylmethyl)ethanamine.

9. A compound of claim 3 which is N,N-diethyl-N'-[4-(1H-imidazol-1-yl)phenyl]-1,2-ethanediamine.

10. A compound of claim 1 which is 1-[4-(1H-imidazol-1-yl)-phenyl]-4-(4-methylpiperidin-1-yl)butanone.

11. A compound of claim 1 which is 4-(Diethylamino)-1-[4-(1H-imidazol-1-yl)phenyl]butanone dihydrochloride.

12. A compound of claim 1 which is α-[4-(1H-imidazol-1-yl)-phenyl]-4-methyl-1-piperidineethanol.

13. A compound of claim 1 which is 4-(1H-imidazol-1-yl)-[((1-methylethyl)amino)methyl]benzenemethanol.

14. A compound of claim 1 which is α-[[ethyl(phenylmethyl)-amino]methyl]-4-(1H-imidazol-1-yl)benzenemethanol.

* * * * *

UNITED STATES PATENT AND TRADEMARK OFFICE
CERTIFICATE OF CORRECTION

PATENT NO. : 4,851,526

DATED : July 25, 1989

INVENTOR(S) : Stanley S. Greenberg, et al.

It is certified that error appears in the above-identified patent and that said Letters Patent is hereby corrected as shown below:

Column 4, line 5

"-4-(2methyl-"   should read   ----- -4-(2-methyl- -----.

Column 10 - Scheme D   No. XXI

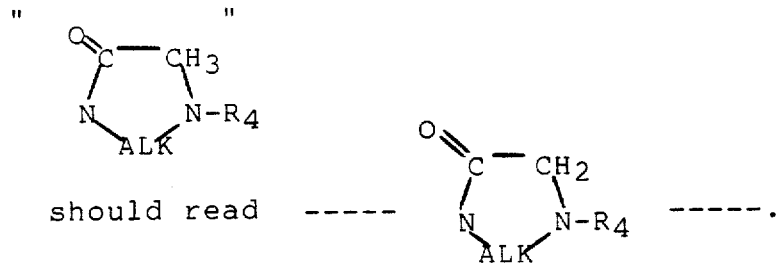

Column 20, line 27

"fluoro4-nitrobenzene"   should read -----fluoro-4-nitrobenzene-----.

Column 21, line 65

"vacuo and 100 mL" should read --vacuo and add 100 mL--.

Column 22, line 68

"fluoro 4-nitrobenzene" should read ----fluoro-4-nitrobenzene----.

UNITED STATES PATENT AND TRADEMARK OFFICE
CERTIFICATE OF CORRECTION

PATENT NO. : 4,851,526

DATED : July 25, 1989

INVENTOR(S) : Stanley S. Greenberg, et al.

It is certified that error appears in the above-identified patent and that said Letters Patent is hereby corrected as shown below:

Column 27, line 6

"[bis(-" should read ---- [bis-( ----.

Column 27, line 28

"2-[bis(-" should read ---- 2-[bis-( ----.

Column 32, line 3

"is allowd" should read ---- is allowed ----.

Column 35, line 34

"1,2 ethanediamine" should read ---- 1,2-ethanediamine ----.

Column 36, line 67

"(1H imidazol" should read ---- (1H-imidazol ----.

Column 37, line 10

"Filter the slats" should read ---- Filter the salts ----.

Column 38, line 45

"[2-Dimethylamino)" should read ---- [2-(Dimethylamino) ----.

Column 40, line 43

"α-(bromomethyl" should read ---- α-(bromomethyl) ----.

UNITED STATES PATENT AND TRADEMARK OFFICE
CERTIFICATE OF CORRECTION

PATENT NO.  : 4,851,526

DATED       : July 25, 1989

INVENTOR(S) : Stanley S. Greenberg, et al.

It is certified that error appears in the above-identified patent and that said Letters Patent is hereby corrected as shown below:

Column 40, line 68

"the resultnat" should read ---- the resultant ----.

Column 41, line 39

"$Ch_2Cl_2$" should read ---- $CH_2Cl_2$ ----.

Signed and Sealed this

Sixteenth Day of April, 1991

*Attest:*

HARRY F. MANBECK, JR.

*Attesting Officer* — *Commissioner of Patents and Trademarks*